United States Patent
Dilly et al.

(10) Patent No.: US 9,585,890 B2
(45) Date of Patent: *Mar. 7, 2017

(54) MODULATORS OF ANDROGEN SYNTHESIS

(71) Applicant: Tangent Reprofiling Limited, London (GB)

(72) Inventors: Suzanne Dilly, Oxfordshire (GB); Gregory Stoloff, London (GB); Paul Taylor, London (GB)

(73) Assignee: Tangent Reprofiling Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/169,610

(22) Filed: May 31, 2016

(65) Prior Publication Data

US 2016/0271134 A1 Sep. 22, 2016

Related U.S. Application Data

(63) Continuation of application No. 14/708,052, filed on May 8, 2015, now Pat. No. 9,375,433, which is a continuation-in-part of application No. 14/037,481, filed on Sep. 26, 2013, now Pat. No. 9,072,743.

(60) Provisional application No. 61/705,790, filed on Sep. 26, 2012, provisional application No. 61/871,662, filed on Aug. 29, 2013, provisional application No. 61/990,800, filed on May 9, 2014.

(51) Int. Cl.

| | |
|---|---|
| *A61K 31/517* | (2006.01) |
| *A61K 31/42* | (2006.01) |
| *A61K 31/20* | (2006.01) |
| *A61K 31/519* | (2006.01) |
| *A61K 31/201* | (2006.01) |
| *A61K 45/06* | (2006.01) |
| *A61K 31/202* | (2006.01) |
| *A61K 31/454* | (2006.01) |

(52) U.S. Cl.
CPC .......... *A61K 31/519* (2013.01); *A61K 31/201* (2013.01); *A61K 31/202* (2013.01); *A61K 31/454* (2013.01); *A61K 45/06* (2013.01)

(58) Field of Classification Search
USPC ................................ 514/258, 378, 379, 560
See application file for complete search history.

(56) References Cited

U.S. PATENT DOCUMENTS

| | | |
|---|---|---|
| 5,723,467 A | 3/1998 | Mesens et al. |
| 6,034,132 A | 3/2000 | Remmereit |
| 6,319,950 B1 * | 11/2001 | Seidel ............... A61K 31/231 514/547 |
| 6,977,271 B1 * | 12/2005 | Ip ..................... A61K 31/20 514/560 |
| 8,153,648 B2 | 4/2012 | Tombari et al. |
| 9,375,433 B2 * | 6/2016 | Dilly ................. A61K 31/519 |
| 2006/0276412 A1 | 12/2006 | Tollefson |
| 2009/0143344 A1 | 6/2009 | Chang |
| 2014/0088120 A1 | 3/2014 | Dilly et al. |

FOREIGN PATENT DOCUMENTS

| | | | |
|---|---|---|---|
| IL | WO 2004103262 A2 * | 12/2004 | ............ A61K 31/00 |
| WO | 0243652 A2 | 6/2002 | |
| WO | 03066039 A1 | 8/2003 | |
| WO | 2005066196 A1 | 7/2005 | |
| WO | 2008034129 A2 | 3/2008 | |
| WO | 2012109387 A1 | 8/2012 | |

OTHER PUBLICATIONS

Okamoto, Y., et al., Journal of Pain and Symptom Management vol. 34 pp. 217-222. Published 2007.*
Goldie-Coldman Theorum. Stedmans Medical Dictionary 27th Edition. Published 2000.*
Reagan-Shaw et al., FASEB J vol. 22 pp. 659-661. Published 2007.*
Konig, M.H., "Starting Risperidal After Clozapine," National Alliance for the Mentally Ill, pp. 1-4, (1995).
Molina, J.R., et al., "Non-Small Cell Lung Cancer: Epidemiology, Risk Factors, Treatment, and Survivorship," Mayo Clin, Proc., vol. 83, pp. 583-594 (2008).
9Z, 11E-conjugated linoleic acid, Chemical Entities of Biological Interest, published 2011.
Brys, et al., "Reconstitution of the Human 5-HT(1D) Receptor-G-Protein Coupling: Evidence for Constitutive Activity and Multiple Receptor Conformations," Mol. Pharmacol. 57(6): 1132-1141 (2000).
Chou, "Theoretical Basism Experimental Design, and Computerized Simulation of Synergism and Antagonism n Drug Combination Studies," Pharmacol. Rev. 58(3): 621-681 (2006).
Cookson, et al., "Prolactin, Hyperprolactinaemia and Antipsychotic Treatment: A Review and Lessons for Treatment of Early Psychosis," Psychopharm, Journal of Psychopharmacology, 2012, 26(5) Supplement 42-51.
David, et al., Cancer Biology and Therapy vol. 99, pp. 678-684, published 2010.

(Continued)

*Primary Examiner* — Timothy Thomas
*Assistant Examiner* — George W Kosturko
(74) *Attorney, Agent, or Firm* — One3 IP Management, P.C.; Dean G. Stathakis; Peter D. Weinstein

(57) ABSTRACT

The present specification discloses compositions comprising at least one therapeutic compound capable of modulating androgen production and methods and uses for treating a disorder associated with androgen production using such compositions and/or compounds.

29 Claims, 2 Drawing Sheets

(56) References Cited

OTHER PUBLICATIONS

Depakote product page. Sanofi, published 2013.
Ichiyama, et al., Brain Research vol. 857, pp. 246-251, published 2000.
Jafari, et al.,"Structural Contributions of Antipsychotic Drugs to their Therapeutic Profiles and Metabolic Side Effects," J. Neurochem. 120: 371-384 (2012).
Kalkman, et al., "Extended Radioligand Binding Profile of Iloperidone: A Broad Spectrum Dopamine/Serotonin/Norepinephrine Receptor Antagonist for the Management of Psychotic Disorders," Neuropsychopharmacol. 25(6): 904-914 (2001).
Kanagarajadura, et al., "Molecular Modeling and Docking Studies of Human 5-Hydroxytryptamine 2A (5-HT2A) Receptor for the Identification of Hotspots for Ligand Binding," Mol. BioSyst. 5: 1877-1888 (2009).
Katzman, et al., Lipids in Health and Disease, vol. 6, pp. 1-4, published 2007.
Kobayashi, et al., "Effect of Altering Dietary ω-6/ω-3 Fatty Acid Ratios on Prostate Cancer Membrane Composition, Cyclooxygenase-2, and Prostaglandin E2," Clin Cancer Res 2006;12:4662-4670. Published Online Aug. 9, 2006.
Leysen, et al., "In vitro and in vivo Receptor Binding and Effects on Monoamine Turnover in Rat Brain Regions of the Novel Antipsychotics Risperidone and Ocaperidone," Mol. Pharmacol. 41(3): 494-508 (1992).
Ochoa, et al., Carcinogenesis vol. 25, pp. 1185-1192, published 2004.
PCT International Search Report and Written Opinion for PCT/EP2013/070106, mailed Jan. 15, 2014.
Refined Sesame Oil, Vitaplant, published 2005.
Wang, et al., Basic and Clinical Pharmacology and Toxicology vol. 13, pp. 336-341, published 2008.
Wei-Lan, Y., et al., "Combination Treatmentof Tamoxifen with Risperidone in Breast Cancer," PLOS One, (Jun. 2014), vol. 9, No. 6.
Wiklund E. D., et al., "Cytotoxic effects of antipsychotic drugs implicate cholesterol homeostasis as a novel chemotherapeutic target," International Journal of Cancer, (Jan. 2010), vol. 126, No. 1, pp. 28-40.
Xia, et al., Cancer Research vol. 66, pp. 7237-7244, published 2006.
Xiao, et al., PNAS vol. 95, pp. 2680-2685, published 1998.
Yong-Min, J., "Mechanisms underlying risperidone-mediated inhibition of cell proliferation in human colon cancer cell line SW480," Shijie Huaren Xiaohua Zazhi, vol. 21, No. 5, pp. 381-85, (2013).

* cited by examiner

MODULATORS OF ANDROGEN SYNTHESIS

This application is a continuation and claims the benefit of priority pursuant to 35 U.S.C. §120 to U.S. patent application Ser. No. 14/708,052, filed on May 8, 2015, a continuation-in-part that claims the benefit of priority to U.S. patent application Ser. No. 14/037,481, filed on Sep. 26, 2013, now U.S. Pat. No. 9,072,743, a U.S. Non-Provisional patent application that claims priority pursuant to 35 U.S.C. §119 (e) to U.S. Provisional application 61/705,790, filed on Sep. 26, 2012 and U.S. Provisional Patent Application 61/871,662, filed on Aug. 29, 2013, and also claims the benefit of priority pursuant to 35 U.S.C. §119(e) to U.S. Patent Application 61/990,800, filed on May 9, 2014, each of which is hereby incorporated by reference in its entirety.

BACKGROUND

Androgen is a generic term for any natural or synthetic compound (often a steroid hormone). Androgens stimulate or control the development and maintenance of male characteristics in vertebrates by binding to androgen receptors. This includes the activity of the accessory male sex organs and development of male secondary sex characteristics. Androgens are also the original anabolic steroids and the precursor of estrogens, the female sex hormones. The androgens include dihydrotestosterone testosterone, androstenedione, androstenediol, and dehydroepiandrosterone.

Certain disorders or disease conditions are exacerbated by the presence of androgens. One such example is a hormone-sensitive or hormone-dependent cancer. A hormone-sensitive or hormone-dependent cancer is one where the proliferation of tumor cells depends on the presence of a hormone or its activity. Non-limiting examples of hormone-dependent cancers include cancers of the breast, endometrium, prostate, ovary, testis, thyroid and bone. Other examples of a hormone-sensitive or hormone-dependent disorder include, without limitation, a non-cancerous cell proliferation disorder like a uterine fibroid, a fibrocystic breast disease, an ovarian cyst, and prostate enlargement; abnormal uterine bleeding, amenorrhoea, premenstrual syndrome (PMS), endometriosis, adenomyosis, and alopecia.

Hormone depletion therapy is the current treatment option available to people diagnosed with certain hormone-sensitive or hormone-dependent disorders, such as, e.g. a hormone-dependent cancer. The basic of this therapy is that growth of a cancer can be reduced or halted by starving tumor cells of a hormone inducing cell proliferation. Typically, this is achieved by reducing the overall systemic levels of a hormone, by preventing the endogenous hormone from interacting with its cognate receptor, or both. Although effective at first, most hormone dependent cancers become refractory after one to three years and resume growth despite continued hormone depletion therapy. Once a hormone-sensitive or hormone-dependent disorder becomes hormone refractory, the treatment options available to a patient are limited.

Thus, there is a still exists a need for the development of pharmaceutical compositions and/or therapeutic compounds effective at treating a disorder associated with androgen production.

SUMMARY

Aspects of the present specification disclose compositions comprising a therapeutic compound capable of modulating androgen production. Therapeutic compounds include, without limitation, a benzo(iso)oxazolepiperidine, a fatty acid, a 5α reductase inhibitor, a chemotherapeutic agent, an anti-proliferative agent, or any combination thereof. The composition disclosed herein may reduce an unwanted side and/or reduce a symptom of a disorder associated with androgen production.

Aspects of the present specification also disclose methods of treating an individual with a disorder associated with androgen production. The disclosed methods comprising the step of administering to an individual in need thereof a pharmaceutical composition disclosed herein, wherein administration reduces a symptom of a disorder associated with androgen production. A disorder associated with androgen production may be a disorder associated with steroid hydroxy-dehydrogenase activity, a disorder associated with HSD17B activity, a disorder associated with HSD17B10 activity, or any combination thereof. A disorder associated with androgen production may be a hormone-dependent disorder like a hormone-dependent proliferative disorder or a hormone-dependent non-proliferative disorder. A disorder associated with androgen production may be a cancer, a hormone-refractory cancer, benign prostatic hyperplasia (BPH), polycystic ovary syndrome, acne vulgaris, seborrhea, female hirsutism, or androgenic alopecia. Administration of a pharmaceutical composition may reduce the frequency of a symptom, the number of symptoms, the severity of a symptom, or any combination thereof. Administration of a pharmaceutical composition may also reduce an unwanted side in the individual.

Aspects of the present specification disclose uses of the disclosed compositions and/or therapeutic compounds in the manufacture of a medicament for the treatment of a disorder associated with androgen production.

Aspects of the present specification disclose uses of the disclosed compositions and/or therapeutic compounds in the treatment of a disorder associated with androgen production.

DETAILED DESCRIPTION

Figure 1:
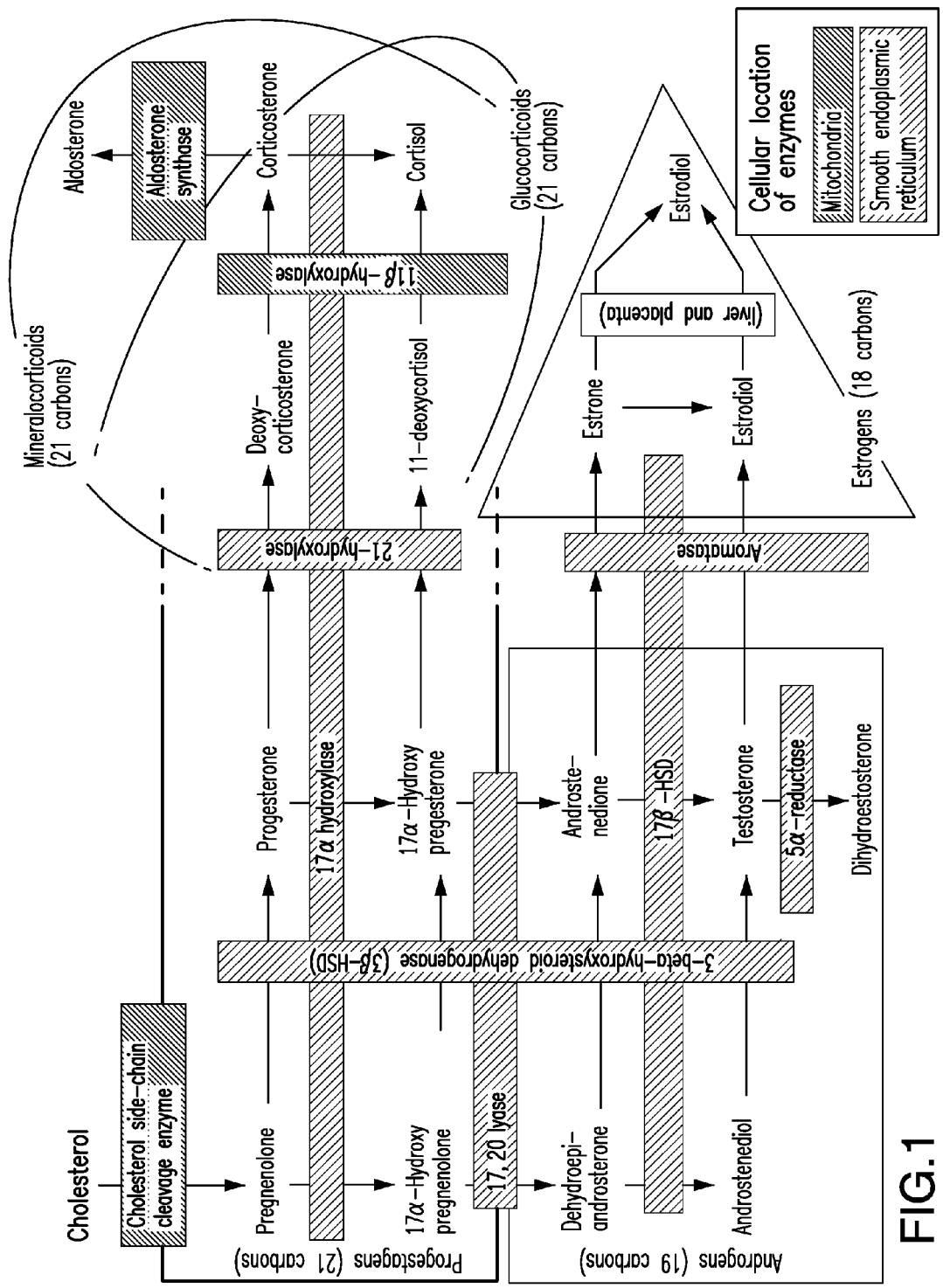
FIG. 1 shows the steroidogenesis pathway for sex hormones, including the enzymes involved in the pathway.

Many patients treated with a hormone depletion therapy become resistant to this therapy. The present specification discloses that one possible mechanism for why certain hormone-sensitive or hormone-dependent disorders become refractory is the presence of a secondary pathway that produces the hormone or hormonal activity targeted for depletion. For example, prostate cancer is a hormone-dependent cancer and patients diagnosed with this cancer are typically treated using an androgen depletion therapy. However, many such patients become refractory to this treatment after one to three years. One possible explanation for this treatment resistance is the presence of an additional pathway that becomes responsible for generating testosterone (or dihydrotestosterone) in a manner useful to support proliferation of prostate tumor cells.

The present specification discloses compounds and pharmaceutical compositions comprising compounds that produce therapeutic effects in reducing a symptom of a disorder associated with androgen production. In aspects of this embodiment, the therapeutic effect is achieved by reducing or inhibiting the activity facilitated by an alternative or secondary pathway responsible for androgen production. In aspects of this embodiment, the therapeutic effect is achieved by reducing or inhibiting the activity facilitated by the primary pathway responsible for androgen production in addition to reducing or inhibiting the activity facilitated by an alternative or secondary pathway responsible for androgen production.

Aspects of the present specification disclose, in part, a pharmaceutical composition. As used herein, the term "pharmaceutical composition" is synonymous with "pharmaceutically acceptable composition" and refers to a therapeutically effective concentration of an active ingredient, such as, e.g., any of the therapeutic compounds disclosed herein. As used herein, the term "pharmaceutically acceptable" refers to any molecular entity or composition that does not produce an adverse, allergic or other untoward or unwanted reaction when administered to an individual. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may comprise one or more therapeutic compounds disclosed herein. In one embodiment, pharmaceutical composition disclosed herein may comprise only a single a therapeutic disclosed herein. In another embodiment, pharmaceutical composition disclosed herein may comprise a plurality of therapeutic compounds disclosed herein. In aspects of this embodiment, a pharmaceutical composition disclosed herein comprises at least one therapeutic compound, at least two therapeutic compounds, at least three therapeutic compounds, or at least four therapeutic compounds. In other aspects of this embodiment, a pharmaceutical composition disclosed herein comprises at most two therapeutic compounds, at most three therapeutic compounds, or at most four therapeutic compounds. In yet other aspects of this embodiment, a pharmaceutical composition disclosed herein comprises one to three therapeutic compounds, two to four therapeutic compounds, two to five therapeutic compounds, three to five therapeutic compounds, or two to three therapeutic compounds.

A pharmaceutical composition disclosed herein may reduce the occurrence of an unwanted side effect elicited by administration of one or more of the therapeutic compounds contained in the pharmaceutical composition. Examples of an unwanted side effect, include, without limitation, feminization in males and defeminisation of females. Examples of male feminization include, without limitation, chemical castration, decreased erections, reduced sexual desire, bone pain, breast tenderness, gynaecomastia, hot flushes, weight gain, gastrointestinal disorders, fatigue, headache, depression, nausea, hepatic changes including elevated levels of transaminases and jaundice. Examples of female defeminisation include, without limitation, unwanted hair growth, increased risk for developing osteoporosis and joint disorders such as arthritis, arthrosis and arthralgia, infertility, aggressive behaviour, adrenal insufficiency, kidney failure, and liver dysfunction.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. Any suitable form of a therapeutic compound may be chosen. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may also be provided as prodrug or active metabolite.

A therapeutic compound disclosed herein may reduce a symptom of a disorder associated with androgen production by, e.g., reducing a steroid hydroxy-dehydrogenase activity, reducing a 11β-hydroxysteroid dehydrogenase activity, reducing a symptom of a disorder associated with a 3β-hydroxysteroid dehydrogenase activity, reducing a 17β-hydroxysteroid dehydrogenase activity, reducing a 20β-hydroxysteroid dehydrogenase activity, or any combination thereof. A therapeutic compound disclosed herein may reduce a symptom of a disorder associated with androgen production by, e.g., reducing a level or an activity of a dihydrotestosterone, reducing a level or an activity of a testosterone, reducing a level or an activity of an androstenedione, reducing a level or an activity of an androstenediol, reducing a level or an activity of a dehydroepiandrosterone, or any combination thereof.

In one embodiment, a therapeutic compound disclosed herein reduces a symptom of a disorder associated with androgen production. In aspects of this embodiment, a therapeutic compound disclosed herein reduces a symptom of a disorder associated with androgen production by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a symptom of a disorder associated with androgen production by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the frequency of a symptom of a disorder associated with androgen production incurred over a given time period. In aspects of this embodiment, a therapeutic compound disclosed herein reduces the frequency of a symptom of a disorder associated with androgen production incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the frequency of a symptom of a disorder associated with androgen production incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the number of symptoms of a disorder associated with androgen production incurred over a given time period. In aspects of this embodiment, a therapeutic compound disclosed herein reduces the number of symptoms of a disorder associated with androgen production incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the number of symptoms of a disorder associated with androgen production incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the severity of a symptom of a disorder associated with androgen production. In aspects of this embodiment, a therapeutic compound disclosed herein reduces the severity of a symptom of a disorder associated with androgen production by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the severity of a symptom of a disorder associated with androgen production by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In one embodiment, a therapeutic compound disclosed herein reduces a symptom of a disorder associated with steroid hydroxy-dehydrogenase activity. In aspects of this embodiment, a therapeutic compound disclosed herein reduces a symptom of a disorder associated with steroid hydroxy-dehydrogenase activity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a symptom of a disorder associated with steroid hydroxy-dehydrogenase activity by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the frequency of a symptom of a disorder associated with steroid hydroxy-dehydrogenase activity incurred over a given time period. In aspects of this embodiment, a therapeutic compound disclosed herein reduces the frequency of a symptom of a disorder associated with steroid hydroxy-dehydrogenase activity incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the frequency of a symptom of a disorder associated with steroid hydroxy-dehydrogenase activity incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the number of symptoms of a disorder associated with steroid hydroxy-dehydrogenase activity incurred over a given time period. In aspects of this embodiment, a therapeutic compound disclosed herein reduces the number of symptoms of a disorder associated with steroid hydroxy-dehydrogenase activity incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the number of symptoms of a disorder associated with steroid hydroxy-dehydrogenase activity incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the severity of a symptom of a disorder associated with steroid hydroxy-dehydrogenase activity. In aspects of this embodiment, a therapeutic compound disclosed herein reduces the severity of a symptom of a disorder associated with steroid hydroxy-dehydrogenase activity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the severity of a symptom of a disorder associated with steroid hydroxy-dehydrogenase activity by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound disclosed herein may be capable of modulating 17β-Hydroxysteroid dehydrogenase (HSD17B) activity. As used herein, the term "capable of modulating HSD17B activity" refers to the ability of the therapeutic compound disclosed herein to directly or indirectly alter the oxidative activity of a HSD17B, directly or indirectly alter the reductive activity of a HSD17B, directly or indirectly decrease the level of a progesterone in an individual, directly or indirectly decrease the level of an androgen in an individual, directly or indirectly decrease the level of an estrogen in an individual, or any combination thereof. Steroid hydroxy-dehydrogenases are a class of enzyme involved in androgen production. 17β-hydroxysteroid dehydrogenases (17β HSDs or HSD17Bs) are responsible for oxidation and reduction of androgens via this bio-synthetic pathway. Most of these enzymes are capable of working in both redox directions, but predominantly carry out one reaction in vivo. HSD17β10 (HSD17B10 or HSD10) is known to be up-regulated in certain cancers as well as cancer that have become hormone refractory.

In aspects of this embodiment, a therapeutic compound capable of modulating HSD17B activity includes, without limitation, a therapeutic compound capable of modulating HSD17B subtype 1 (HSD17B1) activity a therapeutic compound capable of modulating HSD17B subtype 2 (HSD17B2) activity a therapeutic compound capable of modulating HSD17B subtype 3 (HSD17B3) activity a therapeutic compound capable of modulating HSD17B subtype 4 (HSD17B4) activity a therapeutic compound capable of modulating HSD17B subtype 5 (HSD17B5) activity a therapeutic compound capable of modulating HSD17B subtype 6 (HSD17B6) activity a therapeutic compound capable of modulating HSD17B subtype 7 (HSD17B7) activity a therapeutic compound capable of modulating HSD17B subtype 8 (HSD17B8) activity a therapeutic compound capable of modulating HSD17B subtype 9 (HSD17B9) activity a therapeutic compound capable of modulating HSD17B subtype 10 (HSD17B10) activity a therapeutic compound capable of modulating HSD17B subtype 11 (HSD17B11) activity a therapeutic compound capable of modulating HSD17B subtype 12 (HSD17B12) activity a therapeutic compound capable of modulating HSD17B subtype 13 (HSD17B13) activity a therapeutic compound capable of modulating HSD17B subtype 14 (HSD17B14) or a therapeutic compound capable of modulating HSD17B subtype 15 (HSD17B15) activity.

In one embodiment, a therapeutic compound disclosed herein reduces a symptom of a disorder associated with HSD17B activity. In aspects of this embodiment, a therapeutic compound disclosed herein reduces a symptom of a disorder associated with HSD17B activity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a symptom of a disorder associated with HSD17B activity by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the frequency of a symptom of a disorder associated with HSD17B activity incurred over a given time period. In aspects of this embodiment, a therapeutic compound disclosed herein reduces the frequency of a symptom of a disorder associated with HSD17B activity incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the frequency of a symptom of a disorder associated with HSD17B activity incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the number of symptoms of a disorder associated with HSD17B activity incurred over a given time period. In aspects of this embodiment, a therapeutic compound disclosed herein reduces the number of symptoms of a disorder associated with HSD17B activity incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the number of symptoms of a disorder associated with HSD17B activity incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the severity of a symptom of a disorder associated with HSD17B activity. In aspects of this embodiment, a therapeutic compound disclosed herein reduces the severity of a symptom of a disorder associated with HSD17B activity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the severity of a symptom of a disorder associated with HSD17B activity by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces the severity of a symptom of a disorder associated with HSD17B10 (or HSD10) enzymatic activity. In aspects of this embodiment, a therapeutic compound disclosed herein reduces the severity of a symptom of a disorder associated with HSD17B10 enzymatic activity by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces the severity of a symptom of a disorder associated with HSD17B10 enzymatic activity by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein modulates androgen production. In aspects of this embodiment, a therapeutic compound disclosed herein modulates androgen production by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein modulates androgen production by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%. In yet other aspects of this embodiment, modulation of androgen production may include modulation of a steroid hydroxy-dehydrogenase activity. In still other aspects of this embodiment, modulation of androgen production may include a 11β-hydroxysteroid dehydrogenase activity, a 3β-hydroxysteroid dehydrogenase activity, a 17β-hydroxysteroid dehydrogenase activity, a 20β-hydroxysteroid dehydrogenase activity, or any combination thereof.

In another embodiment, a therapeutic compound disclosed herein reduces a level of a dihydrotestosterone. In aspects of this embodiment, a therapeutic compound disclosed herein reduces a level of a dihydrotestosterone by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a level of a dihydrotestosterone by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces a level of a testosterone. In aspects of this embodiment, a therapeutic compound disclosed herein reduces a level of a testosterone by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a level of a testosterone by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces a level of an androstenedione. In aspects of this embodiment, a therapeutic compound disclosed herein reduces a level of an androstenedione by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a level of an androstenedione by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces a level of an androstenediol. In aspects of this embodiment, a therapeutic compound disclosed herein reduces a level of an androstenediol by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a level of an androstenediol by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces a level of a dehydroepiandrosterone (DHEA). In aspects of this embodiment, a therapeutic compound disclosed herein reduces a level of a DHEA by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a level of a DHEA by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein reduces a level of an estrogen. In aspects of this embodiment, a therapeutic compound disclosed herein reduces a level of an estrogen by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein reduces a level of an estrogen by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein is a benzo(iso)oxazolepiperidine. Benzo(iso)oxazolepiperidines are a family of antipsychotic drugs. In aspects of this embodiment, a benzo(iso)oxazolepiperidine may be Iloperidone {1-[4-[3-[4-(6-fluoro-1,2-benzoxazol-3-yl)piperidin-1-yl]propoxy]-3-methoxyphenyl]ethanone}, ocaperidone {3-[2-[4-(6-fluoro-1,2-benzoxazol-3-yl)piperidin-1-yl]ethyl]-2,9-dimethylpyrido[1,2-a]pyrimidin-4-one}, paliperidone or 9-hydroxyrisperidone {3-[2-[4-[6-fluorobenzo[d]isoxazol-3-yl)-1-piperidyl]ethyl]-7-hydroxy-4-methyl-1,5-diazabicyclo[4.4.0]deca-3,5-dien-2-one}, and risperidone {3-[2-[4-(6-fluoro-1,2-benzoxazol-3-yl)piperidin-1-yl]ethyl]-2-methyl-6,7,8,9-tetrahydropyrido[1,2-a]pyrimidin-4-one}.

In an embodiment, a therapeutic compound disclosed herein is compound I or an optionally substituted compound I.

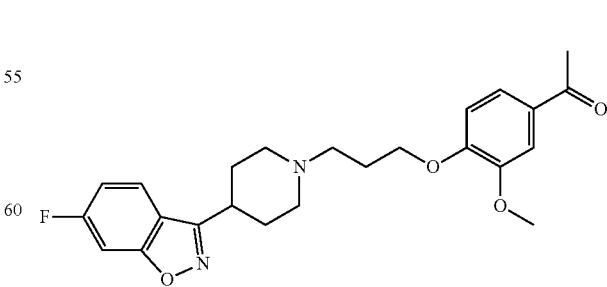

I

In some embodiment, a therapeutic compound disclosed herein is compound II or an optionally substituted compound II.

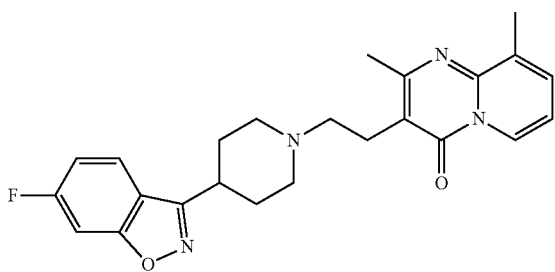

In some embodiment, a therapeutic compound disclosed herein is compound III or an optionally substituted compound III.

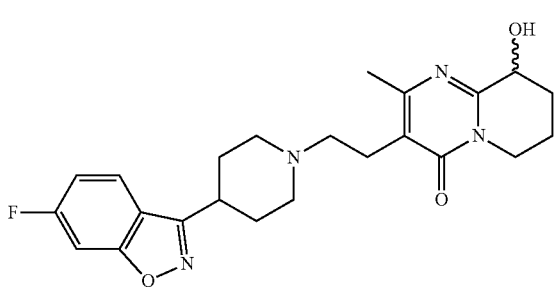

In some embodiment, a therapeutic compound disclosed herein is compound IV or an optionally substituted compound IV.

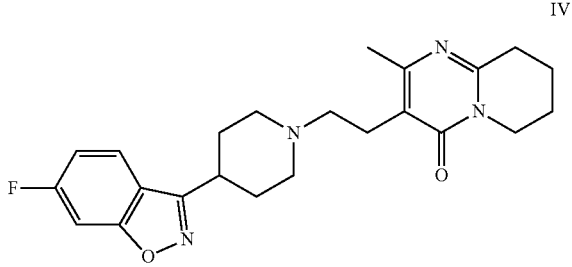 [SMILES: Cc1nc2n(c(=O)c1CCN1CCC(c3noc4cc(F)ccc34)CC1)CCCC2]

Unless otherwise indicated, when a compound or chemical structural feature disclosed herein is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

In an embodiment, a therapeutic compound disclosed herein is a pharmaceutically-acceptable fatty acid. A fatty acid comprises a carboxylic acid with a long unbranched hydrocarbon chain which may be either saturated or unsaturated. This arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, Capryllic acid, pelargonic acid, Capric acid, Undecylic acid, Lauric acid, Tridecylic acid, Myristic acid, Myristoleic acid, Pentadecyclic acid, Palmitic acid, Palmitoleic acid, Sapienic acid, Margaric acid, Stearic acid, Oleic acid, Elaidic acid, Vaccenic acid, Linoleic acid, Linoelaidic acid, α-Linolenic acid, γ-Linolenic acid, Stearidonic acid, Nonadecylic acid, Arachidic acid, Eicosenoic acid, Dihomo-γ-linolenic acid, Mead acid, Arachidonic acid, Eicosapentaenoic acid, Heneicosylic acid, Behenic acid, Erucic acid, Docosahexaenoic acid, Tricosylic acid, Lignoceric acid, Nervonic acid, Pentacosylic acid, Cerotic acid, Heptacosylic acid, Montanic acid, Nonacosylic acid, Melissic acid, Henatriacontylic acid, Lacceroic acid, Psyllic acid, Geddic acid, Ceroplastic acid, and Hexatriacontylic acid.

In aspects of this embodiment, a saturated or unsaturated fatty acid comprises, e.g., at least 8, at least 10, at least 12, at least 14, at least 16, at least 18, at least 20, at least 22, at least 24, at least 26, at least 28, or at least 30 carbon atoms, In other aspects of this embodiment, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

In another embodiment, an adjuvant may comprise one kind of pharmaceutically-acceptable fatty acid. In another embodiment, an adjuvant may comprise a plurality of different pharmaceutically-acceptable fatty acids. In aspects of this embodiment, an adjuvant may comprise, e.g., two or more different fatty acids, three or more different fatty acids, four or more different fatty acids, five or more different fatty acids, or six or more different fatty acids.

A pharmaceutically-acceptable fatty acid useful in the pharmaceutical compositions disclosed herein may be a pharmaceutically-acceptable omega fatty acid. Non-limiting examples of an omega fatty acid include an omega-3 fatty acid, an omega-6 fatty acid, an omega-7 fatty acid, an omega-9 fatty acid. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body. An omega-3 fatty acid includes, without limitation, Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (Clupanodonic acid) (22:5), Docosahexaenoic acid (22:6), Tetracosapentaenoic acid (24:5), Tetracosahexaenoic acid (Nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, Linoleic acid (18:2), γ-linolenic acid (18:3), Calendic acid (18:3), Eicosadienoic acid (20:2), Dihomo-γ-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5).

Omega-7 fatty acids (also known as n-7 fatty acids or ω-7 fatty acids) are a family of unsaturated fatty acids that have in common a final carbon-carbon double bond in the n-7 position, that is, the seventh bond, counting from the methyl end of the fatty acid. An omega-7 fatty acid includes, without limitation, 5-Dodecenoic acid (12:1), 7-Tetradecenoic acid (14:1), 9-Hexadecenoic acid (Palmitoleic acid) (16:1), 11-Decenoic acid (Vaccenic acid) (18:1), 9Z,11E conjugated Linoleic acid (Rumenic acid)(18:2), 13-Eicosenoic acid (Paullinic acid) (20:1), 15-Docosenoic acid (22:1), and 17-Tetracosenoic acid (24:1).

Omega-9 fatty acids (also known as n-9 fatty acids or ω-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, Oleic acid (18:1), Elaidic acid (18:1), Eicosenoic acid (20:1), Mead acid (20:3), Erucic acid (22:1), Nervonic acid (24:1), and Ricinoleic acid.

A pharmaceutically-acceptable fatty acid useful in the pharmaceutical compositions disclosed herein may be a pharmaceutically-acceptable conjugated fatty acid. Conjugated fatty acids are positional and geometric isomers of polyunsaturated fatty acids in which at least one pair of double bonds are separated by only one single bond. In one aspect of this embodiment, a pharmaceutically-acceptable conjugated fatty acid is, e.g., a C16 conjugated fatty acid, a C18 conjugated fatty acid, a C20 conjugated fatty acid, a C22 conjugated fatty acid, a C24 conjugated fatty acid, a C26 conjugated fatty acid, a C28 conjugated fatty acid or a C30 conjugated fatty acid. In one aspect of this embodiment, pharmaceutically-acceptable conjugated fatty acid is, e.g., a C16-C18 conjugated fatty acid, a C16-C20 conjugated fatty acid, a C16-C22 conjugated fatty acid, a C16-C24 conjugated fatty acid, a C16-C26 conjugated fatty acid, a C16-C28 conjugated fatty acid, a C16-C30 conjugated fatty acid, a C18-C20 conjugated fatty acid, a C18-C22 conjugated fatty acid, a C18-C24 conjugated fatty acid, a C18-C26 conjugated fatty acid, a C18-C28 conjugated fatty acid, a C18-C30 conjugated fatty acid, a C20-C22 conjugated fatty acid, a C20-C24 conjugated fatty acid, a C20-C26 conjugated fatty acid, a C20-C28 conjugated fatty acid, a C20-C30 conjugated fatty acid, a C22-C24 conjugated fatty acid, a C22-C26 conjugated fatty acid, a C22-C28 conjugated fatty acid, a C22-C30 conjugated fatty acid, a C24-C26 conjugated fatty acid, a C24-C28 conjugated fatty acid, a C24-C30 conjugated fatty acid, a C26-C28 conjugated fatty acid, a C26-C30 conjugated fatty acid, or C28-C30 conjugated fatty acid.

In another aspect of this embodiment, a pharmaceutically-acceptable conjugated fatty acid includes, e.g., a conjugated Linoleic acid, a conjugated Linoelaidic acid, a conjugated α-Linolenic acid, a conjugated γ-Linolenic acid, a conjugated Calendic acid, a conjugated Eicosadienoic acid, a conjugated Stearidonic acid, a conjugated Nonadecylic acid, a conjugated Arachidic acid, a conjugated Dihomo-γ-linolenic acid, a conjugated Docosadienoic, a conjugated Mead acid, a conjugated Arachidonic acid, a conjugated Eicosapentaenoic acid, a conjugated Adrenic acid, a conjugated Docosapentaenoic acid, a conjugated Heneicosylic acid, a conjugated Tetracosatetraenoic acid, a conjugated Tetracosapentaenoic acid, a conjugated Behenic acid, a conjugated Docosahexaenoic acid, a conjugated Tricosylic acid, a conjugated Lignoceric acid, a conjugated Pentacosylic acid, a conjugated Cerotic acid, a conjugated Heptacosylic acid, a conjugated Montanic acid, a conjugated Nonacosylic acid, a conjugated Melissic acid, a conjugated Henatriacontylic acid, a conjugated Lacceroic acid, a conjugated Psyllic acid, a conjugated Geddic acid, a conjugated Ceroplastic acid, a conjugated Hexatriacontylic acid, or any combination thereof.

A pharmaceutically-acceptable fatty acid useful in the pharmaceutical compositions disclosed herein may be a pharmaceutically-acceptable conjugated linoleic acid (CLA). Conjugated linoleic acid (CLA) refers to a group of at least 28 positional and geometric isomers of linoleic acid (cis-9, cis-12, octadecadienoic acid). The double bonds of CLAs are conjugated, with only one single bond between them. Virtually all cis- and trans-isomeric combinations of CLA have been identified. A CLA includes, without limitation, cis-9, trans-11, conjugated linoleic acid (c-9, t-11 CLA), cis-9, cis-11, conjugated linoleic acid (c-9, c-11 CLA), trans-9, trans-11, conjugated linoleic acid (t-9, t-11 CLA), and trans-9, cis-11, conjugated linoleic acid (t-9, c-11 CLA), cis-10, trans-12, conjugated linoleic acid (c-10, t-12 CLA), cis-10, cis-12, conjugated linoleic acid (c-10, c-12 CLA), trans-10, trans-12, conjugated linoleic acid (t-10, t-12 CLA), and trans-10, cis-12, conjugated linoleic acid (t-10, c-12 CLA), or any combination thereof.

In an embodiment, a therapeutic compound disclosed herein is a 5α reductase inhibitor. The enzyme 5α-reductase is involved in the conversion of testosterone to the active form dihydrotestosterone (DHT) by reducing the Δ4,5 double-bond. In benign prostatic hyperplasia, dihydrotestosterone acts as a potent cellular androgen and promotes prostate growth; therefore, inhibiting the enzyme reduces the excessive prostate growth. In alopecia, male-pattern baldness is one of the effects of androgenic receptor activation. Thus, reducing the levels of dihydrotestosterone reduces alopecia. These inhibitors decrease the levels of available 5α-reductase prior to testosterone's binding with the enzyme, thus reducing levels of dihydrotestosterone that derives from such a bond. A 5α reductase inhibitor include, without limitation, Alfatradiol, Bexlosteride, Dutasteride, Epristeride, Finasteride, Isotretinoin, Lapisteride, Turosteride In an embodiment, a therapeutic compound disclosed herein is a chemotherapeutic agent or an anti-proliferative agent. A chemotherapeutic agent or other anti-proliferative agent include, without limitation, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycin, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCI), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), azaepothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+.sup.32P (Isotope Solutions), 06 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP- 005 (Peplin Biotech), MGV (Progenics), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

Depending upon the particular condition, or disease, to be treated, additional therapeutic agents that are normally administered to treat that condition may also be present in the compositions disclosed herein. As used herein, additional therapeutic agents that are normally administered to treat a particular disease, or condition, are known as "appropriate for the disease, or condition, being treated".

In an embodiment, a pharmaceutical composition comprises a benzo(iso)oxazolepiperidine and a fatty acid. In an aspect of this embodiment, a pharmaceutical composition comprises a benzo(iso)oxazolepiperidine and an Omega-3 fatty acid. In another aspect of this embodiment, a pharmaceutical composition comprises a benzo(iso)oxazolepiperidine and an Omega-6 fatty acid. In yet another aspect of this embodiment, a pharmaceutical composition comprises a benzo(iso)oxazolepiperidine and an Omega-7 fatty acid. In still another aspect of this embodiment, a pharmaceutical composition comprises a benzo(iso)oxazolepiperidine and an Omega-9 fatty acid. In other aspects, a pharmaceutical composition comprises Risperidone and an Omega-3 fatty acid, an Omega-6 fatty acid, an Omega-7 fatty acid, an Omega-9 fatty acid, or any combination thereof. In yet other aspects, a pharmaceutical composition comprises Risperidone and α-Linolenic acid, Arachidonic acid, Docosahexaenoic acid, Rumenic acid, or any combination thereof.

In an embodiment, a pharmaceutical composition comprises a benzo(iso)oxazolepiperidine and a fatty acid where there is a synergistic effect between the benzo(iso)oxazolepiperidine and the fatty acid. In an aspect of this embodiment, a pharmaceutical composition comprises a benzo(iso)oxazolepiperidine and an Omega-3 fatty acid where there is a synergistic effect between the benzo(iso)oxazolepiperidine and the Omega-3 fatty acid. In another aspect of this embodiment, a pharmaceutical composition comprises a benzo(iso)oxazolepiperidine and an Omega-6 fatty acid where there is a synergistic effect between the benzo(iso)oxazolepiperidine and the Omega-6 fatty acid. In yet another aspect of this embodiment, a pharmaceutical composition comprises a benzo(iso)oxazolepiperidine and an Omega-7 fatty acid where there is a synergistic effect between the benzo(iso)oxazolepiperidine and the Omega-7 fatty acid. In still another aspect of this embodiment, a pharmaceutical composition comprises a benzo(iso)oxazolepiperidine and an Omega-9 fatty acid where there is a synergistic effect between the benzo(iso)oxazolepiperidine and the Omega-9 fatty acid. In other aspects, a pharmaceutical composition comprises Risperidone and an Omega-3 fatty acid, an Omega-6 fatty acid, an Omega-7 fatty acid, an Omega-9 fatty acid, or any combination thereof where there is a synergistic effect between the benzo(iso)oxazolepiperidine and the Omega-3 fatty acid, the Omega-6 fatty acid, the Omega-7 fatty acid, the Omega-9 fatty acid, or any combination thereof. In yet other aspects, a pharmaceutical composition comprises Risperidone and α-Linolenic acid, Arachidonic acid, Docosahexaenoic acid, Rumenic acid, or any combination thereof.

In an embodiment, a pharmaceutical composition comprises a benzo(iso)oxazolepiperidine in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg and a fatty acid like an Omega-3 fatty acid, an Omega-6 fatty acid, an Omega-7 fatty acid, an Omega-9 fatty acid, or any combination thereof in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg.

In an embodiment, a pharmaceutical composition comprises a benzo(iso)oxazolepiperidine in an amount of at least 0.1 mg, at least 0.2 mg, at least 0.3 mg, at least 0.4 mg, at least 0.5 mg, at least 0.6 mg, at least 0.7 mg, at least 0.8 mg, at least 0.9 mg, at least 1 mg, at least 2 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, at least 15 mg, at least 16 mg, at least 17 mg, at least 18 mg, at least 19 mg, or at least 20 mg and a fatty acid like an Omega-3 fatty acid, an Omega-6 fatty acid, an Omega-7 fatty acid, an Omega-9 fatty acid, or any combination thereof in an amount of at least 0.1 mg, at least 0.2 mg, at least 0.3 mg, at least 0.4 mg, at least 0.5 mg, at least 0.6 mg, at least 0.7 mg, at least 0.8 mg, at least 0.9 mg, at least 1 mg, at least 2 mg, at least 3 mg, at least 4 mg, at least 5 mg, at least 6 mg, at least 7 mg, at least 8 mg, at least 9 mg, at least 10 mg, at least 11 mg, at least 12 mg, at least 13 mg, at least 14 mg, at least 15 mg, at least 16 mg, at least 17 mg, at least 18 mg, at least 19 mg, or at least 20 mg.

In an embodiment, a pharmaceutical composition comprises a benzo(iso)oxazolepiperidine in an amount of at most 0.1 mg, at most 0.2 mg, at most 0.3 mg, at most 0.4 mg, at most 0.5 mg, at most 0.6 mg, at most 0.7 mg, at most 0.8 mg, at most 0.9 mg, at most 1 mg, at most 2 mg, at most 3 mg, at most 4 mg, at most 5 mg, at most 6 mg, at most 7 mg, at most 8 mg, at most 9 mg, at most 10 mg, at most 11 mg, at most 12 mg, at most 13 mg, at most 14 mg, at most 15 mg, at most 16 mg, at most 17 mg, at most 18 mg, at most 19 mg, or at most 20 mg and a fatty acid like an Omega-3 fatty acid, an Omega-6 fatty acid, an Omega-7 fatty acid, an Omega-9 fatty acid, or any combination thereof in an amount of at most 0.1 mg, at most 0.2 mg, at most 0.3 mg, at most 0.4 mg, at most 0.5 mg, at most 0.6 mg, at most 0.7 mg, at most 0.8 mg, at most 0.9 mg, at most 1 mg, at most 2 mg, at most 3 mg, at most 4 mg, at most 5 mg, at most 6 mg, at most 7 mg, at most 8 mg, at most 9 mg, at most 10 mg, at most 11 mg, at most 12 mg, at most 13 mg, at most 14 mg, at most 15 mg, at most 16 mg, at most 17 mg, at most 18 mg, at most 19 mg, or at most 20 mg.

In an embodiment, a pharmaceutical composition comprises a benzo(iso)oxazolepiperidine in an amount of about 0.1 mg to about 1 mg, about 0.1 mg to about 5 mg, about 0.1 mg to about 10 mg, about 0.1 mg to about 15 mg, about 0.1 mg to about 20 mg, about 0.5 mg to about 1 mg, about 0.5 mg to about 5 mg, about 0.5 mg to about 10 mg, about 0.5 mg to about 15 mg, about 0.5 mg to about 20 mg, about 1 mg to about 5 mg, about 1 mg to about 10 mg, about 1 mg to about 15 mg, about 1 mg to about 20 mg, about 5 mg to about 10 mg, about 5 mg to about 15 mg, about 5 mg to about 20 mg, about 10 mg to about 15 mg, about 10 mg to about 20 mg, or about 15 mg to about 20 mg, and a fatty acid like an Omega-3 fatty acid, an Omega-6 fatty acid, an Omega-7 fatty acid, an Omega-9 fatty acid, or any combination thereof in an amount of about 0.1 mg to about 1 mg, about 0.1 mg to about 5 mg, about 0.1 mg to about 10 mg, about 0.1 mg to about 15 mg, about 0.1 mg to about 20 mg, about 0.5 mg to about 1 mg, about 0.5 mg to about 5 mg, about 0.5 mg to about 10 mg, about 0.5 mg to about 15 mg, about 0.5 mg to about 20 mg, about 1 mg to about 5 mg, about 1 mg to about 10 mg, about 1 mg to about 15 mg, about 1 mg to about 20 mg, about 5 mg to about 10 mg, about 5 mg to about 15 mg, about 5 mg to about 20 mg, about 10 mg to about 15 mg, about 10 mg to about 20 mg, or about 15 mg to about 20 mg.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, flavoring agents, coloring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

A therapeutic compound disclosed herein, or a composition comprising such a therapeutic compound, may be formulated for either local or systemic delivery using topical, enteral or parenteral routes of administration. Additionally, a therapeutic compound disclosed herein may be formulated by itself in a pharmaceutical composition, or may be formulated together with one or more other therapeutic compounds disclosed herein in a single pharmaceutical composition.

A therapeutic compound disclosed herein, or a composition comprising such a therapeutic compound, may be made into an inhaled formulation. Inhaled formulations suitable for enteral or parenteral administration include, without limitation, aerosols, dry powders. A therapeutic compound or composition disclosed herein intended for such administration may be prepared according to any method known to the art for the manufacture of pharmaceutical compositions.

In such inhaled dosage forms, the therapeutic compound may be prepared for delivery as an aerosol in a liquid propellant for use in a pressurised (PDI) or other metered dose inhaler (MDI). Propellants suitable for use in a PDI or MDI include, without limitation, CFC-12, HFA-134a, HFA- 227, HCFC-22 (difluorochloromethane), HFA-152 (difluoroethane and isobutane). A therapeutic compound may also be delivered using a nebulisers or other aerosol delivery system. A therapeutic compound may be prepared for delivery as a dry powder for use in a dry powder inhaler (DPI). A dry powder for use in the inhalers will usually have a mass median aerodynamic diameter of less than 30 pm, preferably less than 20 pm and more preferably less than 10 pm. Microparticles having aerodynamic diameters in the range of about 5 pm to about 0.5 pm will generally be deposited in the respiratory bronchioles, whereas smaller particles, having aerodynamic diameters in the range of about 2 pm to about 0.05 pm, are likely to be deposited in the alveoli. A DPI may be a passive delivery mechanism, which relies on the individual's inspiration to introduce the particles into the lungs, or an active delivery mechanism, requiring a mechanism for delivering the powder to the individual. In inhalatory formulations, a therapeutically effective amount of a therapeutic compound disclosed herein for an inhaled formulation may be between about 0.0001% (w/v) to about 60% (w/v), about 0.001% (w/v) to about 40.0% (w/v), or about 0.01% (w/v) to about 20.0% (w/v). In inhalatory formulations, a therapeutically effective amount of a therapeutic compound disclosed herein for an inhaled formulation may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a solid formulation. Solid formulations suitable for enteral or parenteral administration include, without limitation, capsules, tablets, pills, troches, lozenges, powders and granules suitable for inhalation or for reconstitution into sterile injectable solutions or dispersions. A therapeutic compound or composition disclosed herein intended for such administration may be prepared according to any method known to the art for the manufacture of pharmaceutical compositions. In such solid dosage forms, the therapeutic compound may be admixed with (a) at least one inert customary excipient (or carrier), such as, e.g., sodium citrate or dicalcium phosphate or (b) fillers or extenders, as for example, starch, lactose, sucrose, glucose, mannitol, isomalt, and silicic acid, (c) binders, such as, e.g., carboxymethylcellulose, alignates, gelatin, polyvinylpyrrolidone, sucrose and acacia, (d) humectants, such as, e.g., glycerol, (e) disintegrating agents, such as, e.g., agar-agar, calcium carbonate, corn starch, potato starch, tapioca starch, alginic acid, certain complex silicates and sodium carbonate, (f) solution retarders, such as, e.g., paraffin, (g) absorption accelerators, such as, e.g., quaternary ammonium compounds, (h) wetting agents, such as, e.g., cetyl alcohol and glycerol monostearate, (i) adsorbents, such as, e.g., kaolin and bentonite, (j) lubricants, such as, e.g., talc, stearic acid, calcium stearate, magnesium stearate, solid polyethylene glycols, sodium lauryl sulfate or mixtures thereof, and (k) buffering agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In solid formulations, a therapeutically effective amount of a therapeutic compound disclosed herein typically may be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a semi-solid formulation. Semi-solid formulations suitable for topical administration include, without limitation, ointments, creams, salves, and gels. A therapeutic compound or composition disclosed herein intended for such administration may be prepared according to any method known to the art for the manufacture of pharmaceutical compositions. In semi-solid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v). In semi-solid formulations, a therapeutically effective amount of a therapeutic compound disclosed herein typically may also be between about 0.0001% (w/w) to about 60% (w/w), about 0.001% (w/w) to about 40.0% (w/w), or about 0.01% (w/w) to about 20.0% (w/w).

A therapeutic compound disclosed herein, or a composition comprising such a therapeutic compound, may be made into a liquid formulation. Liquid formulations suitable for enteral or parenteral administration include, without limitation, solutions, syrups, elixirs, dispersions, emulsions, and suspensions. A therapeutic compound or composition disclosed herein intended for such administration may be prepared according to any method known to the art for the manufacture of pharmaceutical compositions. In such liquid dosage forms, a therapeutic compound or composition disclosed herein may be admixed with (a) suitable aqueous and nonaqueous carriers, (b) diluents, (c) solvents, such as, e.g., water, ethanol, propylene glycol, polyethyleneglycol, glycerol, vegetable oils, such as, e.g., rapeseed oil and olive oil, and injectable organic esters such as ethyl oleate; and/or fluidity agents, such as, e.g., surfactants or coating agents like lecithin. In the case of dispersions and suspensions, fluidity can also be controlled by maintaining a particular particle size. In liquid formulations, a therapeutically effective amount of a therapeutic compound disclosed herein typically may be between about 0.0001% (w/v) to about 60% (w/v), about 0.001% (w/v) to about 40.0% (w/v), or about 0.01% (w/v) to about 20.0% (w/v).

Syrups and elixirs may be formulated with sweetening agents, for example glycerol, propylene glycol, sorbitol or sucrose. Such formulations may also contain a demulcent, a preservative, flavoring agents, and coloring agents.

Liquid suspensions may be formulated by suspending a therapeutic compound disclosed herein in admixture with excipients suitable for the manufacture of aqueous suspensions. Such excipients are suspending agents, for example sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate.

Oily suspensions may be formulated by suspending a therapeutic compound disclosed herein in admixture with (a) vegetable oils, such as, e.g., almond oil, *arachis* oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof, (b) a saturated fatty acid, an unsaturated fatty acid, or a combination thereof, such as, e.g., palmitic acid, stearic acid, oleic acid, linoleic acid, linolenic acid, or a combination thereof, (c) mineral oil such as, e.g., liquid paraffin, (d) surfactants or detergents. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the combined therapeutic compounds in admixture with a dispersing or wetting agent, suspending agent and one or more preservatives.

A therapeutic compound disclosed herein may be in the form of oil-in-water emulsions. The oily phase may be a vegetable oil as disclosed herein or a mineral oil as disclosed herein or mixtures thereof. Suitable emulsifying agents may be naturally occurring gums, such as, e.g., gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

A therapeutic compound disclosed herein, or a composition comprising such a therapeutic compound, may also be incorporated into a drug delivery platform in order to achieve a controlled release profile over time. Such a drug delivery platform comprises a therapeutic compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hyrophilic and Hydrophobic Agents, U.S. Pat. No. 7,048,946; Hughes, et. al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. Patent Publication 2011/0008437; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a therapeutic compound disclosed herein over a period of about seven days or more. As used herein, the term "extended release" refers to the release of a therapeutic compound disclosed herein over a period of time of less than about seven days.

In aspects of this embodiment, a sustained release drug delivery platform releases a therapeutic compound disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a therapeutic compound disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a sustained release drug delivery platform releases a therapeutic compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a therapeutic compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a therapeutic compound disclosed herein with substantially zero order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a therapeutic compound disclosed herein with substantially zero order release kinetics over a period of, e.g., at most 1 day after administration, at most 2 days after administration, at most 3 days after administration, at most 4 days after administration, at most 5 days after administration, or at most 6 days after administration.

In aspects of this embodiment, a drug delivery platform releases a therapeutic compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a therapeutic compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

Aspects of the present specification disclose, in part, a method of treating an individual with a disorder associated with androgen production. In one embodiment, the method comprises the step of administering to an individual in need thereof a benzo(iso)oxazolepiperidine disclosed herein and a pharmaceutically-acceptable conjugated fatty acid disclosed herein, wherein administration reduces a symptom of a disorder associated with androgen production, thereby treating the individual. The benzo(iso)oxazolepiperidine disclosed herein and a pharmaceutically-acceptable conjugated fatty acid disclosed herein may be administered sequentially or simultaneously. When administered simultaneously, the benzo(iso)oxazolepiperidine disclosed herein and a pharmaceutically-acceptable conjugated fatty acid disclosed herein may be formulated as separate compositions or as a single composition. In one embodiment, the method comprises the step of administering to an individual in need thereof a pharmaceutical composition disclosed herein, wherein administration reduces a symptom of a disorder associated with androgen production, thereby treating the individual. In aspects of this embodiment, a disorder associated with androgen production includes, without limitation, a disorder associated with steroid hydroxy-dehydrogenase activity, a disorder associated with HSD17B activity, and a disorder associated with HSD17B10 activity.

Aspects of the present specification disclose, in part, a method of treating an individual with a cancer. In one embodiment, the method comprises the step of administering to an individual in need thereof a benzo(iso)oxazolepiperidine disclosed herein and a pharmaceutically-acceptable conjugated fatty acid disclosed herein, wherein administration reduces a symptom of a cancer, thereby treating the individual. The benzo(iso)oxazolepiperidine disclosed herein and a pharmaceutically-acceptable conjugated fatty acid disclosed herein may be administered sequentially or simultaneously. When administered simultaneously, the benzo(iso)oxazolepiperidine disclosed herein and a pharmaceutically-acceptable conjugated fatty acid disclosed herein may be formulated as separate compositions or as a single composition. In one embodiment, the method comprises the step of administering to an individual in need thereof a pharmaceutical composition disclosed herein, wherein administration reduces a symptom of a cancer, thereby treating the individual.

In one embodiment, a disorder associated with androgen production may be a hormone-sensitive or hormone-dependent disorder, such as, e.g., a hormone-sensitive or hormone-dependent cancer, a hormone-sensitive or hormone-dependent non-cancerous cell proliferation disorder, or a hormone-sensitive or hormone-dependent non-cell proliferation disorder. Examples of a hormone-sensitive or hormone-dependent cancer include, without limitation, a prostate cancer, a testicular cancer, a breast cancer, an endometrial cancer, an ovarian cancer, a lung cancer, a thyroid cancer, a pancreatic cancer, an adenocarcinoma, a neuroendocrine cancer, and a bone cancer. Examples of a hormone-sensitive or hormone-dependent non-cancerous cell proliferation disorder include, without limitation, a uterine fibroid, a fibrocystic breast disease, an ovarian cyst, a polycystic ovary syndrome, and prostate enlargement like benign prostatic hyperplasia (BPH). Examples of a hormone-sensitive or hormone-dependent non-cell proliferation disorder include, without limitation, an acne vulgaris, a seborrhea, a female hirsutism, abnormal uterine bleeding, amenorrhoea, premenstrual syndrome (PMS), endometriosis, adenomyosis, and an alopecia.

An adenocarcinoma is a tumor of epithelial tissue that has glandular origin, glandular characteristics, or both. Examples of an adenocarcinoma include, without limitation, an esophageal cancer, a pancreatic cancer, a prostate cancer, a cervical cancer, a stomach cancer, a throat cancer, a non-small cell lung cancer, a ductal carcinoma of the breast including invasive ductal carcinoma and ductal carcinoma in situ, a lobular carcinoma of the breast including an invasive lobular carcinoma, a colorectal cancer, adenocarcinoma of the lung including large cell lung cancer, squamous cell lung cancer, small-cell lung cancer, bronchioloalveolar lung cancer, non-small cell lung cancer, cholangiocarcinoma and vaginal cancer.

Aspects of the present specification disclose, in part, treating an individual suffering from a disorder associated with androgen production. As used herein, the term "treating," refers to reducing or eliminating in an individual a clinical symptom of a disorder associated with androgen production; or delaying or preventing in an individual the onset of a clinical symptom of a disorder associated with androgen production. For example, the term "treating" can mean reducing a symptom of a disorder associated with androgen production by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. As another example, the term "treating" can mean controlling a symptom of a disorder associated with androgen production such as, e.g., reducing the number of symptoms per given time period and/or the severity of a symptom. The actual symptoms associated with a disorder associated with androgen production are well known and can be determined by a person of ordinary skill in the art by taking into account factors, including, without limitation, the location of the disorder associated with androgen production, the cause of the disorder associated with androgen production, the severity of the disorder associated with androgen production, and/or the cells, tissue or organ affected by the disorder associated with androgen production. Those of skill in the art will know the appropriate symptoms or indicators associated with a specific type of a disorder associated with androgen production and will know how to determine if an individual is a candidate for treatment as disclosed herein.

The actual symptoms of a disorder associated with androgen production are well known and can be determined by a person of ordinary skill in the art by taking into account factors, including, without limitation, the location of the disorder associated with androgen production, the cause of the disorder associated with androgen production, the severity of the disorder associated with androgen production, the cell, tissue and/or organ affected by the disorder associated with androgen production. For example, a disorder associated with androgen production may cause one or more of the following symptoms: urinary hesitancy, frequent urination, dysuria (painful urination), increased risk of urinary tract infections, and urinary retention, abnormal bleeding, inflammation, abnormal hair growth, pain, sexual dysfunction.

Aspects of the present invention provide, in part, reducing a symptom associated with a hormone-sensitive or hormone-dependent cancer. A treatment using the disclosed therapeutic compounds and compositions disclosed herein may decrease the growth rate of tumor cells, decrease the cell division rate of tumor cells, decrease the extent of invasion of tumor cells into adjacent tissue or organs, decrease the extent of metastasis, decrease angiogenesis, increase apoptosis, increase tumor cell death, increase tumor cell necrosis, or any combination thereof.

Aspects of the present invention provide, in part, reducing a symptom associated with a hormone-sensitive or hormone-dependent non-cancerous cell proliferation disorder. A treatment using the disclosed therapeutic compounds and compositions disclosed herein may decrease hyperplasia, decrease the growth rate of hyperproliferating cells, decrease the cell division rate of hyperproliferating cells, decrease the extent to which hyperproliferating cells becomes cancerous, decrease angiogenesis, decrease nodule formation, decrease cyst formation, increase apoptosis, increase tumor cell death and/or increase tumor cell necrosis, or any combination thereof.

Aspects of the present invention provide, in part, reducing a symptom associated with a hormone-sensitive or hormone-dependent non-cancerous cell proliferation disorder. A treatment using the disclosed therapeutic compounds and compositions disclosed herein may improve at least one hair attribute including, without limitation, increase hair length, increase hair thickness, increase new hair growth, increase hair growth rate, increase hair number, increase conversion of intermediate hair into terminal hair, increase hair density, increase number of hairs per follicle, and/or increase hair pigmentation, increase hair melanization, or any combination thereof.

A composition or compound is administered to an individual. An individual is typically a human being. Typically, any individual who is a candidate for a conventional treatment is a candidate for a disorder associated with androgen production treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to treating a disorder associated with androgen production refers to the minimum dose of a therapeutic compound disclosed herein necessary to achieve the desired therapeutic effect and includes a dose sufficient to reduce a symptom associated with a disorder associated with androgen production. The effectiveness of a therapeutic compound disclosed herein in treating a disorder associated with androgen production can be determined by observing an improvement in an individual based upon one or more clinical symptoms, and/or physiological indicators associated with the disorder associated with androgen production. An improvement in a disorder associated with androgen production also can be indicated by a reduced need for a concurrent therapy.

The appropriate effective amount of a therapeutic compound disclosed herein to be administered to an individual for a particular disorder associated with androgen production can be determined by a person of ordinary skill in the art by taking into account factors, including, without limitation, the type of the disorder associated with androgen production, the location of the disorder associated with androgen production, the cause of the disorder associated with androgen production, the severity of the disorder associated with androgen production, the degree of relief desired, the duration of relief desired, the particular therapeutic compound used, the rate of excretion of the therapeutic compound used, the pharmacodynamics of the therapeutic compound used, the nature of the other compounds to be included in the composition, the particular formulation desired, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

Wide variations in the necessary effective amount are to be expected in view of the differing efficiencies of the various routes of administration. For instance, oral administration of a therapeutic compound disclosed herein generally would be expected to require higher dosage levels than administration by inhalation. Similarly, systemic administration of a therapeutic compound disclosed herein would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a therapeutic compound disclosed herein that is administered can be adjusted accordingly.

In aspects of this embodiment, a therapeutically effective amount of a therapeutic compound disclosed herein reduces a symptom associated with a disorder associated with androgen production by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a disorder associated with androgen production by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a disorder associated with androgen production by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In aspects of this embodiment, a therapeutically effective amount of a therapeutic compound disclosed herein generally is in the range of about 0.01 mg/kg/day to about 50 mg/kg/day. In other aspects of this embodiment, an effective amount of a therapeutic compound disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, at least 10 mg/kg/day, at least 25 mg/kg/day, or at least 50 mg/kg/day. In yet other aspects of this embodiment, an effective amount of a therapeutic compound disclosed herein may be, e.g., at least 0.1 mg/kg/day, at least 0.2 mg/kg/day, at least 0.3 mg/kg/day, at least 0.4 mg/kg/day, at least 0.5 mg/kg/day, at least 0.6 mg/kg/day, at least 0.7 mg/kg/day, at least 0.8 mg/kg/day, at least 0.9 mg/kg/day, at least 1.0 mg/kg/day, at least 1.25 mg/kg/day, at least 1.5 mg/kg/day, at least 1.75 mg/kg/day, at least 2.0 mg/kg/day, at least 2.25 mg/kg/day, at least 2.5 mg/kg/day, at least 2.75 mg/kg/day, at least 3.0 mg/kg/day, at least 3.25 mg/kg/day, at least 3.5 mg/kg/day, at least 3.75 mg/kg/day, at least 4.0 mg/kg/day, at least 4.25 mg/kg/day, at least 4.5 mg/kg/day, at least 4.75 mg/kg/day, or at least 5.0 mg/kg/day. In yet other aspects of this embodiment, an effective amount of a therapeutic compound disclosed herein may be, e.g., about 0.01 mg/kg/day to about 0.1 mg/kg/day, about 0.01 mg/kg/day to about 0.5 mg/kg/day, about 0.01 mg/kg/day to about 1 mg/kg/day, about 0.01 mg/kg/day to about 5 mg/kg/day, about 0.01 mg/kg/day to about 10 mg/kg/day, about 0.1 mg/kg/day to about 0.1 mg/kg/day, about 0.1 mg/kg/day to about 0.5 mg/kg/day, about 0.1 mg/kg/day to about 1 mg/kg/day, about 0.1 mg/kg/day to about 5 mg/kg/day, or about 0.1 mg/kg/day to about 10 mg/kg/day.

In aspects of this embodiment, a therapeutically effective amount of a therapeutic compound disclosed herein generally is in the range of about 1 mg/day to about 500 mg/day. In other aspects of this embodiment, an effective amount of a therapeutic compound disclosed herein may be, e.g., at least 1 mg/day, at least 5 mg/day, at least 10 mg/day, at least 25 mg/day, at least 50 mg/day, at least 75 mg/day, at least 100 mg/day, at least 150 mg/day, at least 200 mg/day, at least 250 mg/day, at least 300 mg/day, at least 350 mg/day, at least 400 mg/day, at least 450 mg/day, or at least 500 mg/day. In yet other aspects of this embodiment, an effective amount of a therapeutic compound disclosed herein may be, e.g., about 1 mg/day to about 100 mg/day, about 1 mg/day to about 150 mg/day, about 1 mg/day to about 200 mg/day, about 1 mg/day to about 250 mg/day, about 1 mg/day to about 300 mg/day, about 1 mg/day to about 350 mg/day, about 1 mg/day to about 400 mg/day, about 1 mg/day to about 450 mg/day, about 1 mg/day to about 500 mg/day, about 10 mg/day to about 100 mg/day, about 10 mg/day to about 150 mg/day, about 10 mg/day to about 200 mg/day, about 10 mg/day to about 250 mg/day, about 10 mg/day to about 300 mg/day, about 10 mg/day to about 350 mg/day, about 10 mg/day to about 400 mg/day, about 10 mg/day to about 450 mg/day, or about 10 mg/day to about 500 mg/day.

In aspects of this embodiment, a therapeutically effective amount of a therapeutic compound disclosed herein generally is in the range of about 1 µM/day to about 1,000 µM/day. In other aspects of this embodiment, an effective amount of a therapeutic compound disclosed herein may be, e.g., at least 1 µM/day, at least 5 µM/day, at least 10 µM/day, at least 50 µM/day, at least 100 µM/day, at least 200 µM/day, at least 300 µM/day, at least 400 µM/day, at least 500 µM/day, at least 600 µM/day, at least 700 µM/day, at least 800 µM/day, at least 900 µM/day, or at least 1,000 µM/day. In yet other aspects of this embodiment, an effective amount of a therapeutic compound disclosed herein may be, e.g., about 1 µM/day to about 100 µM/day, about 1 µM/day to about 200 µM/day, about 1 µM/day to about 400 µM/day, about 1 µM/day to about 600 µM/day, about 1 µM/day to about 800 µM/day, about 1 µM/day to about 1,000 µM/day, about 10 µM/day to about 100 µM/day, about 10 µM/day to about 200 µM/day, about 10 µM/day to about 400 µM/day, about 10 µM/day to about 600 µM/day, about 10 µM/day to about 800 µM/day, about 10 µM/day to about 1,000 µM/day, about 25 µM/day to about 100 µM/day, about 25 µM/day to about 200 µM/day, about 25 µM/day to about 400 µM/day, about 25 µM/day to about 600 µM/day, about 25 µM/day to about 800 µM/day, or about 25 µM/day to about 1,000 µM/day.

In aspects of this embodiment, a therapeutically effective amount of a benzo(iso)oxazolepiperidine disclosed herein generally is in the range of about 0.01 mg/kg/day to about 10 mg/kg/day. In other aspects of this embodiment, an effective amount of a benzo(iso)oxazolepiperidine disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, or at least 10 mg/kg/day. In yet other aspects of this embodiment, an effective amount of a benzo(iso)oxazolepiperidine disclosed herein may be, e.g., about 0.01 mg/kg/day to about 0.1 mg/kg/day, about 0.01 mg/kg/day to about 0.25 mg/kg/day, about 0.01 mg/kg/day to about 0.5 mg/kg/day, about 0.01 mg/kg/day to about 0.75 mg/kg/day, about 0.01 mg/kg/day to about 1 mg/kg/day, about 0.01 mg/kg/day to about 1 mg/kg/day, about 0.01 mg/kg/day to about 2.5 mg/kg/day, about 0.01 mg/kg/day to about 5 mg/kg/day, about 0.01 mg/kg/day to about 10 mg/kg/day, about 0.05 mg/kg/day to about 0.1 mg/kg/day, about 0.05 mg/kg/day to about 0.25 mg/kg/day, about 0.05 mg/kg/day to about 0.5 mg/kg/day, about 0.05 mg/kg/day to about 0.75 mg/kg/day, about 0.05 mg/kg/day to about 1 mg/kg/day, about 0.05 mg/kg/day to about 1 mg/kg/day, about 0.05 mg/kg/day to about 2.5 mg/kg/day, about 0.05 mg/kg/day to about 5 mg/kg/day, about 0.05 mg/kg/day to about 10 mg/kg/day, about 0.1 mg/kg/day to about 0.25 mg/kg/day, about 0.1 mg/kg/day to about 0.5 mg/kg/day, about 0.1 mg/kg/day to about 0.75 mg/kg/day, about 0.1 mg/kg/day to about 1 mg/kg/day, about 0.1 mg/kg/day to about 2.5 mg/kg/day, about 0.1 mg/kg/day to about 5 mg/kg/day, about 0.1 mg/kg/day to about 10 mg/kg/day, about 0.5 mg/kg/day to about 0.75 mg/kg/day, about 0.5 mg/kg/day to about 1 mg/kg/day, about 0.5 mg/kg/day to about 2.5 mg/kg/day, about 0.5 mg/kg/day to about 5 mg/kg/day, or about 0.5 mg/kg/day to about 10 mg/kg/day.

In aspects of this embodiment, a therapeutically effective amount of a benzo(iso)oxazolepiperidine disclosed herein generally is in the range of about 0.1 mg/day to about 100 mg/day. In other aspects of this embodiment, an effective amount of a benzo(iso)oxazolepiperidine disclosed herein may be, e.g., at least 0.1 mg/day, at least 0.5 mg/day, at least 1 mg/day, at least 2.5 mg/day, at least 5 mg/day, at least 7.5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, or at least 100 mg/day. In yet other aspects of this embodiment, an effective amount of a benzo(iso)oxazolepiperidine disclosed herein may be, e.g., about 0.1 mg/day to about 10 mg/day, about 0.1 mg/day to about 12.5 mg/day, about 0.1 mg/day to about 15 mg/day, about 0.1 mg/day to about 17.5 mg/day, about 0.1 mg/day to about 20 mg/day, about 0.1 mg/day to about 30 mg/day, about 0.1 mg/day to about 40 mg/day, about 0.1 mg/day to about 60 mg/day, about 0.1 mg/day to about 80 mg/day, about 0.1 mg/day to about 100 mg/day, about 0.5 mg/day to about 10 mg/day, about 0.5 mg/day to about 12.5 mg/day, about 0.5 mg/day to about 15 mg/day, about 0.5 mg/day to about 17.5 mg/day, about 0.5 mg/day to about 20 mg/day, about 0.5 mg/day to about 30 mg/day, about 0.5 mg/day to about 40 mg/day, about 0.5 mg/day to about 60 mg/day, about 0.5 mg/day to about 80 mg/day, about 0.5 mg/day to about 100 mg/day, about 1 mg/day to about 10 mg/day, about 1 mg/day to about 12.5 mg/day, about 1 mg/day to about 15 mg/day, about 1 mg/day to about 17.5 mg/day, about 1 mg/day to about 20 mg/day, about 1 mg/day to about 30 mg/day, about 1 mg/day to about 40 mg/day, about 1 mg/day to about 60 mg/day, about 1 mg/day to about 80 mg/day, about 1 mg/day to about 100 mg/day, about 2.5 mg/day to about 10 mg/day, about 2.5 mg/day to about 20 mg/day, about 2.5 mg/day to about 40 mg/day, about 2.5 mg/day to about 60 mg/day, about 2.5 mg/day to about 80 mg/day, or about 2.5 mg/day to about 100 mg/day.

In aspects of this embodiment, a therapeutically effective amount of a benzo(iso)oxazolepiperidine disclosed herein generally is in the range of about 1 µM/day to about 1,000 µM/day. In other aspects of this embodiment, an effective amount of a benzo(iso)oxazolepiperidine disclosed herein may be, e.g., at least 1 µM/day, at least 5 µM/day, at least 10 µM/day, at least 50 µM/day, at least 100 µM/day, at least 200 µM/day, at least 300 µM/day, at least 400 µM/day, at least 500 µM/day, at least 600 µM/day, at least 700 µM/day, at least 800 µM/day, at least 900 µM/day, or at least 1,000 µM/day. In yet other aspects of this embodiment, an effective amount of a benzo(iso)oxazolepiperidine disclosed herein may be, e.g., about 1 µM/day to about 100 µM/day, about 1 µM/day to about 200 µM/day, about 1 µM/day to about 400 µM/day, about 1 µM/day to about 600 µM/day, about 1 µM/day to about 800 µM/day, about 1 µM/day to about 1,000 µM/day, about 10 µM/day to about 100 µM/day, about 10 µM/day to about 200 µM/day, about 10 µM/day to about 400 µM/day, about 10 µM/day to about 600 µM/day, about 10 µM/day to about 800 µM/day, about 10 µM/day to about 1,000 µM/day, about 25 µM/day to about 100 µM/day, about 25 µM/day to about 200 µM/day, about 25 µM/day to about 400 µM/day, about 25 µM/day to about 600 µM/day, about 25 µM/day to about 800 µM/day, or about 25 µM/day to about 1,000 µM/day.

In aspects of this embodiment, in conjunction with a benzo(iso)oxazolepiperidine disclosed herein, a therapeutically effective amount of a fatty acid disclosed herein generally is in the range of about 0.01 mg/kg/day to about 10 mg/kg/day. In other aspects of this embodiment, in conjunction with a benzo(iso)oxazolepiperidine disclosed herein, an effective amount of a fatty acid disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, or at least 10 mg/kg/day. In yet other aspects of this embodiment, in conjunction with a benzo(iso)oxazolepiperidine disclosed herein, an effective amount of a fatty acid disclosed herein may be, e.g., about 0.01 mg/kg/day to about 0.1 mg/kg/day, about 0.01 mg/kg/day to about 0.25 mg/kg/day, about 0.01 mg/kg/day to about 0.5 mg/kg/day, about 0.01 mg/kg/day to about 0.75 mg/kg/day, about 0.01 mg/kg/day to about 1 mg/kg/day, about 0.01 mg/kg/day to about 1 mg/kg/day, about 0.01 mg/kg/day to about 2.5 mg/kg/day, about 0.01 mg/kg/day to about 5 mg/kg/day, about 0.01 mg/kg/day to about 10 mg/kg/day, about 0.05 mg/kg/day to about 0.1 mg/kg/day, about 0.05 mg/kg/day to about 0.25 mg/kg/day, about 0.05 mg/kg/day to about 0.5 mg/kg/day, about 0.05 mg/kg/day to about 0.75 mg/kg/day, about 0.05 mg/kg/day to about 1 mg/kg/day, about 0.05 mg/kg/day to about 1 mg/kg/day, about 0.05 mg/kg/day to about 2.5 mg/kg/day, about 0.05 mg/kg/day to about 5 mg/kg/day, about 0.05 mg/kg/day to about 10 mg/kg/day, about 0.1 mg/kg/day to about 0.25 mg/kg/day, about 0.1 mg/kg/day to about 0.5 mg/kg/day, about 0.1 mg/kg/day to about 0.75 mg/kg/day, about 0.1 mg/kg/day to about 1 mg/kg/day, about 0.1 mg/kg/day to about 2.5 mg/kg/day, about 0.1 mg/kg/day to about 5 mg/kg/day, about 0.1 mg/kg/day to about 10 mg/kg/day, about 0.5 mg/kg/day to about 0.75 mg/kg/day, about 0.5 mg/kg/day to about 1 mg/kg/day, about 0.5 mg/kg/day to about 2.5 mg/kg/day, about 0.5 mg/kg/day to about 5 mg/kg/day, or about 0.5 mg/kg/day to about 10 mg/kg/day.

In aspects of this embodiment, in conjunction with a benzo(iso)oxazolepiperidine disclosed herein, a therapeutically effective amount of a fatty acid disclosed herein generally is in the range of about 0.1 mg/day to about 100 mg/day. In other aspects of this embodiment, an effective amount of a fatty acid disclosed herein may be, e.g., at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, or at least 100 mg/day. In yet other aspects of this embodiment, in conjunction with a benzo(iso)oxazolepiperidine disclosed herein may be, e.g., about 0.1 mg/day to about 10 mg/day, about 0.1 mg/day to about 12.5 mg/day, about 0.1 mg/day to about 15 mg/day, about 0.1 mg/day to about 17.5 mg/day, about 0.1 mg/day to about 20 mg/day, about 0.1 mg/day to about 30 mg/day, about 0.1 mg/day to about 40 mg/day, about 0.1 mg/day to about 60 mg/day, about 0.1 mg/day to about 80 mg/day, about 0.1 mg/day to about 100 mg/day, about 0.5 mg/day to about 10 mg/day, about 0.5 mg/day to about 12.5 mg/day, about 0.5 mg/day to about 15 mg/day, about 0.5 mg/day to about 17.5 mg/day, about 0.5 mg/day to about 20 mg/day, about 0.5 mg/day to about 30 mg/day, about 0.5 mg/day to about 40 mg/day, about 0.5 mg/day to about 60 mg/day, about 0.5 mg/day to about 80 mg/day, about 0.5 mg/day to about 100 mg/day, about 1 mg/day to about 10 mg/day, about 1 mg/day to about 12.5 mg/day, about 1 mg/day to about 15 mg/day, about 1 mg/day to about 17.5 mg/day, about 1 mg/day to about 20 mg/day, about 1 mg/day to about 30 mg/day, about 1 mg/day to about 40 mg/day, about 1 mg/day to about 60 mg/day, about 1 mg/day to about 80 mg/day, about 1 mg/day to about 100 mg/day, about 2.5 mg/day to about 10 mg/day, about 2.5 mg/day to about 20 mg/day, about 2.5 mg/day to about 40 mg/day, about 2.5 mg/day to about 60 mg/day, about 2.5 mg/day to about 80 mg/day, or about 2.5 mg/day to about 100 mg/day.

In aspects of this embodiment, in conjunction with a benzo(iso)oxazolepiperidine disclosed herein, a therapeutically effective amount of a fatty acid disclosed herein generally is in the range of about 1 µM/day to about 1,000 µM/day. In other aspects of this embodiment, an effective amount of a fatty acid disclosed herein may be, e.g., at least 1 µM/day, at least 5 µM/day, at least 10 µM/day, at least 50 µM/day, at least 100 µM/day, at least 200 µM/day, at least 300 µM/day, at least 400 µM/day, at least 500 µM/day, at least 600 µM/day, at least 700 µM/day, at least 800 µM/day, at least 900 µM/day, or at least 1,000 µM/day. In yet other aspects of this embodiment, in conjunction with a benzo(iso)oxazolepiperidine disclosed herein, an effective amount of a fatty acid disclosed herein may be, e.g., about 1 µM/day to about 100 µM/day, about 1 µM/day to about 200 µM/day, about 1 µM/day to about 400 µM/day, about 1 µM/day to about 600 µM/day, about 1 µM/day to about 800 µM/day, about 1 µM/day to about 1,000 µM/day, about 10 µM/day to about 100 µM/day, about 10 µM/day to about 200 µM/day, about 10 µM/day to about 400 µM/day, about 10 µM/day to about 600 µM/day, about 10 µM/day to about 800 µM/day, about 10 µM/day to about 1,000 µM/day, about 25 µM/day to about 100 µM/day, about 25 µM/day to about 200 µM/day, about 25 µM/day to about 400 µM/day, about 25 µM/day to about 600 µM/day, about 25 µM/day to about 800 µM/day, or about 25 µM/day to about 1,000 µM/day.

In aspects of this embodiment, in conjunction with a benzo(iso)oxazolepiperidine disclosed herein, a therapeutically effective amount of a 5α reductase inhibitor disclosed herein generally is in the range of about 0.01 mg/kg/day to about 10 mg/kg/day. In other aspects of this embodiment, in conjunction with a benzo(iso)oxazolepiperidine disclosed herein, an effective amount of a 5α reductase inhibitor disclosed herein may be, e.g., at least 0.01 mg/kg/day, at least 0.025 mg/kg/day, at least 0.05 mg/kg/day, at least 0.075 mg/kg/day, at least 0.1 mg/kg/day, at least 0.25 mg/kg/day, at least 0.5 mg/kg/day, at least 0.75 mg/kg/day, at least 1.0 mg/kg/day, at least 2.5 mg/kg/day, at least 5.0 mg/kg/day, at least 7.5 mg/kg/day, or at least 10 mg/kg/day. In yet other aspects of this embodiment, in conjunction with a benzo(iso)oxazolepiperidine disclosed herein, an effective amount of a 5α reductase inhibitor disclosed herein may be, e.g., about 0.01 mg/kg/day to about 0.1 mg/kg/day, about 0.01 mg/kg/day to about 0.25 mg/kg/day, about 0.01 mg/kg/day to about 0.5 mg/kg/day, about 0.01 mg/kg/day to about 0.75 mg/kg/day, about 0.01 mg/kg/day to about 1 mg/kg/day, about 0.01 mg/kg/day to about 1 mg/kg/day, about 0.01 mg/kg/day to about 2.5 mg/kg/day, about 0.01 mg/kg/day to about 5 mg/kg/day, about 0.01 mg/kg/day to about 10 mg/kg/day, about 0.05 mg/kg/day to about 0.1 mg/kg/day, about 0.05 mg/kg/day to about 0.25 mg/kg/day, about 0.05 mg/kg/day to about 0.5 mg/kg/day, about 0.05 mg/kg/day to about 0.75 mg/kg/day, about 0.05 mg/kg/day to about 1 mg/kg/day, about 0.05 mg/kg/day to about 1 mg/kg/day, about 0.05 mg/kg/day to about 2.5 mg/kg/day, about 0.05 mg/kg/day to about 5 mg/kg/day, about 0.05 mg/kg/day to about 10 mg/kg/day, about 0.1 mg/kg/day to about 0.25 mg/kg/day, about 0.1 mg/kg/day to about 0.5 mg/kg/day, about 0.1 mg/kg/day to about 0.75 mg/kg/day, about 0.1 mg/kg/day to about 1 mg/kg/day, about 0.1 mg/kg/day to about 2.5 mg/kg/day, about 0.1 mg/kg/day to about 5 mg/kg/day, about 0.1 mg/kg/day to about 10 mg/kg/day, about 0.5 mg/kg/day to about 0.75 mg/kg/day, about 0.5 mg/kg/day to about 1 mg/kg/day, about 0.5 mg/kg/day to about 2.5 mg/kg/day, about 0.5 mg/kg/day to about 5 mg/kg/day, or about 0.5 mg/kg/day to about 10 mg/kg/day.

In aspects of this embodiment, in conjunction with a benzo(iso)oxazolepiperidine disclosed herein, a therapeutically effective amount of a 5α reductase inhibitor disclosed herein generally is in the range of about 0.1 mg/day to about 100 mg/day. In other aspects of this embodiment, in conjunction with a benzo(iso)oxazolepiperidine disclosed herein, an effective amount of a 5α reductase inhibitor disclosed herein may be, e.g., at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, or at least 100 mg/day. In yet other aspects of this embodiment, in conjunction with a benzo(iso)oxazolepiperidine disclosed herein, an effective amount of a 5α reductase inhibitor disclosed herein may be, e.g., about 0.1 mg/day to about 10 mg/day, about 0.1 mg/day to about 12.5 mg/day, about 0.1 mg/day to about 15 mg/day, about 0.1 mg/day to about 17.5 mg/day, about 0.1 mg/day to about 20 mg/day, about 0.1 mg/day to about 30 mg/day, about 0.1 mg/day to about 40 mg/day, about 0.1 mg/day to about 60 mg/day, about 0.1 mg/day to about 80 mg/day, about 0.1 mg/day to about 100 mg/day, about 0.5 mg/day to about 10 mg/day, about 0.5 mg/day to about 12.5 mg/day, about 0.5 mg/day to about 15 mg/day, about 0.5 mg/day to about 17.5 mg/day, about 0.5 mg/day to about 20 mg/day, about 0.5 mg/day to about 30 mg/day, about 0.5 mg/day to about 40 mg/day, about 0.5 mg/day to about 60 mg/day, about 0.5 mg/day to about 80 mg/day, about 0.5 mg/day to about 100 mg/day, about 1 mg/day to about 10 mg/day, about 1 mg/day to about 12.5 mg/day, about 1 mg/day to about 15 mg/day, about 1 mg/day to about 17.5 mg/day, about 1 mg/day to about 20 mg/day, about 1 mg/day to about 30 mg/day, about 1 mg/day to about 40 mg/day, about 1 mg/day to about 60 mg/day, about 1 mg/day to about 80 mg/day, about 1 mg/day to about 100 mg/day, about 2.5 mg/day to about 10 mg/day, about 2.5 mg/day to about 20 mg/day, about 2.5 mg/day to about 40 mg/day, about 2.5 mg/day to about 60 mg/day, about 2.5 mg/day to about 80 mg/day, or about 2.5 mg/day to about 100 mg/day.

In aspects of this embodiment, in conjunction with a benzo(iso)oxazolepiperidine disclosed herein, a therapeutically effective amount of a 5α reductase inhibitor disclosed herein generally is in the range of about 1 µM/day to about 1,000 µM/day. In other aspects of this embodiment, in conjunction with a benzo(iso)oxazolepiperidine disclosed herein, an effective amount of a 5α reductase inhibitor disclosed herein may be, e.g., at least 1 µM/day, at least 5 µM/day, at least 10 µM/day, at least 50 µM/day, at least 100 µM/day, at least 200 µM/day, at least 300 µM/day, at least 400 µM/day, at least 500 µM/day, at least 600 µM/day, at least 700 µM/day, at least 800 µM/day, at least 900 µM/day, or at least 1,000 µM/day. In yet other aspects of this embodiment, in conjunction with a benzo(iso)oxazolepiperidine disclosed herein, an effective amount of a 5α reductase inhibitor disclosed herein may be, e.g., about 1 µM/day to about 100 µM/day, about 1 µM/day to about 200 µM/day, about 1 µM/day to about 400 µM/day, about 1 µM/day to about 600 µM/day, about 1 µM/day to about 800 µM/day, about 1 µM/day to about 1,000 µM/day, about 10 µM/day to about 100 µM/day, about 10 µM/day to about 200 µM/day, about 10 µM/day to about 400 µM/day, about 10 µM/day to about 600 µM/day, about 10 µM/day to about 800 µM/day, about 10 µM/day to about 1,000 µM/day, about 25 µM/day to about 100 µM/day, about 25 µM/day to about 200 µM/day, about 25 µM/day to about 400 µM/day, about 25 µM/day to about 600 µM/day, about 25 µM/day to about 800 µM/day, or about 25 µM/day to about 1,000 µM/day.

Dosing can be single dosage or cumulative (serial dosing), and can be readily determined by one skilled in the art. For instance, treatment of a disorder associated with androgen production may comprise a one-time administration of an effective dose of a pharmaceutical composition disclosed herein. Alternatively, treatment of a disorder associated with androgen production may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Various routes of administration can be useful for administering a therapeutic compound disclosed herein, according to a method of treating a disorder associated with androgen production disclosed herein. A pharmaceutical composition may be administered to an individual by any of a variety of means depending, e.g., on the type of the disorder associated with androgen production to be treated, the location of the disorder associated with androgen production to be treated, the specific therapeutic compound or composition used, or other compound to be included in the composition, and the history, risk factors and symptoms of the individual. As such, topical, enteral or parenteral routes of administration may be suitable for of treating a disorder associated with androgen production disclosed herein and such routes include both local and systemic delivery of a therapeutic compound or composition disclosed herein. Compositions comprising either a single therapeutic compound disclosed herein, or two or more therapeutic compounds disclosed herein are intended for inhaled, topical, intranasal, sublingual, injection, infusion, instillation, rectal and/or vaginal use may be prepared according to any method known to the art for the manufacture of pharmaceutical compositions.

A pharmaceutical composition disclosed herein can be administered to an individual in a single formulation or in separate formulations, for combined, simultaneous or sequential administration. In one embodiment, an individual is administered a first composition comprising a benzo(iso)oxazolepiperidine and a second composition comprising another therapeutic compound like a fatty acid, a 5α-reductase inhibitor, a chemotherapeutic agent, or an anti-proliferative agent. In aspects of this embodiment, an individual is administered a first composition comprising at least one benzo(iso)oxazolepiperidine and a second composition comprising at least one other therapeutic compound like a fatty acid, a 5α-reductase inhibitor, a chemotherapeutic agent, or an anti-proliferative agent.

In another embodiment, an individual is administered a composition comprising a benzo(iso)oxazolepiperidine and another therapeutic compound like a fatty acid, a 5α-reductase inhibitor, a chemotherapeutic agent, or an anti-proliferative agent. In aspects of this embodiment, an individual is administered a composition comprising at least one benzo(iso)oxazolepiperidine and at least one other therapeutic compound like a fatty acid, a 5α-reductase inhibitor, a chemotherapeutic agent, or an anti-proliferative agent.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present specification may also be described as follows:

1. A composition comprising a therapeutic compound capable of modulating androgen production.
2. The composition according to embodiment 1, wherein the therapeutic compound reduces a symptom of a disorder associated with androgen production.
3. The composition according to embodiments 1 or 2, wherein the therapeutic compound reduces a symptom of a disorder associated with androgen production by at least 10%.
4. The composition according to any one of embodiments 1-3, wherein the therapeutic compound reduces the frequency of a symptom of a disorder associated with androgen production incurred over a given time period.
5. The composition according to any one of embodiments 1-4, wherein the therapeutic compound reduces the frequency of a symptom of a disorder associated with androgen production incurred over a given time period by at least 10%.
6. The composition according to any one of embodiments 1-5, wherein the therapeutic compound reduces the number of symptoms of a disorder associated with androgen production incurred over a given time period.
7. The composition according to any one of embodiments 1-6, wherein the therapeutic compound reduces the number of symptoms of a disorder associated with androgen production incurred over a given time period by at least 10%.
8. The composition according to any one of embodiments 1-7, wherein the therapeutic compound reduces the severity of a symptom of a disorder associated with androgen production.
9. The composition according to any one of embodiments 1-8, wherein the therapeutic compound reduces the severity of a symptom of a disorder associated with androgen production by at least 10%.
10. The composition according to any one of embodiments 1-9, wherein the disorder associated with androgen production is a disorder associated with a steroid hydroxydehydrogenase activity.
11. The composition according to any one of embodiments 1-9, wherein the disorder associated with androgen production is a disorder associated with a 11β-hydroxysteroid dehydrogenase activity, a 3β-hydroxysteroid dehydrogenase activity, a 17β-hydroxysteroid dehydrogenase activity, a 20β-hydroxysteroid dehydrogenase activity, or any combination thereof.

12. The composition according to embodiment 11, wherein the disorder associated with a 17β-hydroxysteroid dehydrogenase activity is a 17β-hydroxysteroid dehydrogenase subtype 10 activity.

13. The composition according to any one of embodiments 1-12, wherein the therapeutic compound reduces a level of a dihydrotestosterone.

14. The composition according to any one of embodiments 1-13, wherein the therapeutic compound reduces a level of a dihydrotestosterone by at least 10%.

15. The composition according to any one of embodiments 1-14, wherein the therapeutic compound reduces a level of a testosterone, a level of an androstenedione, a level of an androstenediol, a level of a dehydroepiandrosterone, or any combination thereof.

16. The composition according to any one of embodiments 1-15, wherein the therapeutic compound reduces a level of a level of a testosterone, a level of an androstenedione, a level of an androstenediol, a level of a dehydroepiandrosterone, or any combination thereof by at least 10%.

17. The composition according to any one of embodiments 1-16, wherein the therapeutic compound reduces a level of an estrogen.

18. The composition according to any one of embodiments 1-17, wherein the therapeutic compound reduces a level of an estrogen by at least 10%.

19. The composition according to any one of embodiments 1-18, wherein the therapeutic compound includes a benzo(iso)oxazolepiperidine, a fatty acid, a 5α reductase inhibitor, a chemotherapeutic agent, an anti-proliferative agent, or any combination thereof.

20. The composition according to embodiment 19, wherein the benzo(iso)oxazolepiperidine is an optionally substituted Iloperidone, an optionally substituted ocaperidone, an optionally substituted paliperidone, an optionally substituted risperidone, or any combination thereof.

21. The composition according to embodiment 19, wherein the fatty acid comprises a conjugated fatty acid.

22. The composition according to embodiment 21, wherein the conjugated fatty acid comprises a C16-C30 conjugated fatty acid.

23. The composition according to embodiment 21, wherein the conjugated fatty acid comprises a conjugated Linoleic acid, a conjugated Linoelaidic acid, a conjugated α-Linolenic acid, a conjugated γ-Linolenic acid, a conjugated Calendic acid, a conjugated Eicosadienoic acid, a conjugated Stearidonic acid, a conjugated Nonadecylic acid, a conjugated Arachidic acid, a conjugated Dihomo-γ-linolenic acid, a conjugated Docosadienoic, a conjugated Mead acid, a conjugated Arachidonic acid, a conjugated Eicosapentaenoic acid, a conjugated Adrenic acid, a conjugated Docosapentaenoic acid, a conjugated Heneicosylic acid, a conjugated Tetracosatetraenoic acid, a conjugated Tetracosapentaenoic acid, a conjugated Behenic acid, a conjugated Docosahexaenoic acid, a conjugated Tricosylic acid, a conjugated Lignoceric acid, a conjugated Pentacosylic acid, a conjugated Cerotic acid, a conjugated Heptacosylic acid, a conjugated Montanic acid, a conjugated Nonacosylic acid, a conjugated Melissic acid, a conjugated Henatriacontylic acid, a conjugated Lacceroic acid, a conjugated Psyllic acid, a conjugated Geddic acid, a conjugated Ceroplastic acid, a conjugated Hexatriacontylic acid, or a combination thereof.

24. The composition according to embodiment 23, wherein the conjugated linoleic acid comprises a cis-9, trans-11, conjugated linoleic acid, cis-9, cis-11, conjugated linoleic acid, trans-9, trans-11, conjugated linoleic acid, and trans-9, cis-11, conjugated linoleic acid, cis-10, trans-12, conjugated linoleic acid, cis-10, cis-12, conjugated linoleic acid, trans-10, trans-12, conjugated linoleic acid, and trans-10, cis-12, conjugated linoleic acid, or any combination thereof.

25. The composition according to embodiment 19, wherein the fatty acid is an omega-3 fatty acid, an omega-6 fatty acid, an omega-7 fatty acid, an omega-9 fatty acid, or any combination thereof.

26. The composition according to embodiment 25, wherein the omega-3 fatty acid is Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (Clupanodonic acid) (22:5), Docosahexaenoic acid (22:6), Tetracosapentaenoic acid (24:5), Tetracosahexaenoic acid (Nisinic acid) (24:6), or any combination thereof.

27. The composition according to embodiment 25, wherein the omega-6 fatty acid is Linoleic acid (18:2), γ-linolenic acid (18:3), Calendic acid (18:3), Eicosadienoic acid (20:2), Dihomo-γ-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5), or any combination thereof.

28. The composition according to embodiment 25, wherein the omega-7 fatty acid is 5-Dodecenoic acid, 7-Tetradecenoic acid, 9-Hexadecenoic acid (Palmitoleic acid), 11-Decenoic acid (Vaccenic acid), 13-Eicosenoic acid (Paullinic acid), 15-Docosenoic acid, 17-Tetracosenoic acid, and 9Z,11E conjugated Linoleic acid (Rumenic acid), or any combination thereof.

29. The composition according to embodiment 25, wherein the omega-9 fatty acid Oleic acid, Elaidic acid, Eicosenoic acid, Mead acid, Erucic acid, Nervonic acid, and Ricinoleic acid, or any combination thereof.

30. The composition according to embodiment 19, wherein the 5α reductase inhibitor is Alfatradiol, Bexlosteride, Dutasteride, Epristeride, Finasteride, Isotretinoin, Lapisteride, Turosteride, or any combination thereof.

31. The composition according to embodiment 19, wherein the chemotherapeutic agent or anti-proliferative agent is an alkylating agent, a platinum agent, an antimetabolite, a topoisomerase inhibitor, an antitumor antibiotic, an aromatase inhibitor, a thymidylate synthase inhibitor, a DNA antagonist, farnesyltransferase inhibitor, a pump inhibitor, a histone acetyltransferase inhibitor, a metalloproteinase inhibitor, a ribonucleoside reductase inhibitor, a TNFα agonist, a TNFα antagonist, an endothelin A receptor antagonist, a retinoic acid receptor agonist, an immuno-modulator, a hormonal and antihormonal agent, a photodynamic agent, a tyrosine kinase inhibitor, or any combination thereof.

32. The composition according to any one of embodiments 1-31, wherein the pharmaceutical composition reduces an unwanted side.

33. The composition according to embodiment 32, wherein the unwanted side includes feminization in males or defeminisation of females.

34. The composition according to any one of embodiments 1-29, wherein the modulating activity of the therapeutic compound reduces a symptom of a disorder associated with androgen production.

35. The composition according to embodiment 34, wherein the modulating activity of the therapeutic compound reduces a symptom of a disorder associated with androgen production by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

36. The composition according to embodiment 35, wherein the symptom includes the frequency of a symptom, the number of symptoms, the severity of a symptom, or any combination thereof.

37. The composition according to any one of embodiments 1-36, wherein the disorder associated with androgen production is a hormone-dependent disorder.

38. The composition according to embodiment 37, wherein the hormone-dependent disorder is a hormone-dependent proliferative disorder.

39. The composition according to embodiment 37, wherein the hormone-dependent disorder is a hormone-dependent non-proliferative disorder.

40. The composition according to embodiments 37, wherein the hormone-dependent disorder is a cancer.

41. The composition according to embodiment 40, wherein the cancer is a prostate cancer, a lung cancer, a breast cancer, an ovarian cancer, testicular cancer, an adenocarcinoma, neuroendocrine cancer, or a pancreatic cancer.

42. The composition according to embodiment 40, wherein the cancer is an adenocarcinoma.

43. The composition according to embodiment 42, wherein the adenocarcinoma is an esophageal cancer, a pancreatic cancer, a prostate cancer, a cervical cancer, a stomach cancer, a throat cancer, a non-small cell lung cancer, a ductal carcinoma of the breast including invasive ductal carcinoma and ductal carcinoma in situ, a lobular carcinoma of the breast including an invasive lobular carcinoma, a colorectal cancer, an adenocarcinoma of the lung including large cell lung cancer, squamous cell lung cancer, small-cell lung cancer, bronchioloalveolar lung cancer, and non-small cell lung cancer, a cholangiocarcinoma or a vaginal cancer.

44. The composition according to embodiment 43, wherein the lung cancer is a non-small cell lung cancer.

45. The composition according to embodiment 40, wherein the cancer is a hormone-refractory cancer.

46. The composition according to embodiments 39, wherein the hormone-dependent disorder is benign prostatic hyperplasia (BPH) or polycystic ovary syndrome.

47. The composition according to embodiments 39, wherein the hormone-dependent disorder is acne vulgaris, seborrhea, or female hirsutism.

48. The composition according to embodiments 39, wherein the hormone-dependent disorder is androgenic alopecia.

49. The composition according to any one of embodiments 1-48, wherein the composition includes a benzo(iso)oxazolepiperidine and a fatty acid.

50. The composition according to embodiment 49, wherein the benzo(iso)oxazolepiperidine is an optionally substituted Iloperidone, an optionally substituted ocaperidone, an optionally substituted paliperidone, an optionally substituted risperidone, or any combination thereof.

51. The composition according to embodiment 49 or 50, wherein the fatty acid comprises a conjugated fatty acid.

52. The composition according to embodiment 51, wherein the conjugated fatty acid comprises a C16-C30 conjugated fatty acid.

53. The composition according to embodiment 51, wherein the conjugated fatty acid comprises a conjugated Linoleic acid, a conjugated Linoelaidic acid, a conjugated α-Linolenic acid, a conjugated γ-Linolenic acid, a conjugated Calendic acid, a conjugated Eicosadienoic acid, a conjugated Stearidonic acid, a conjugated Nonadecylic acid, a conjugated Arachidic acid, a conjugated Dihomo-γ-linolenic acid, a conjugated Docosadienoic, a conjugated Mead acid, a conjugated Arachidonic acid, a conjugated Eicosapentaenoic acid, a conjugated Adrenic acid, a conjugated Docosapentaenoic acid, a conjugated Heneicosylic acid, a conjugated Tetracosatetraenoic acid, a conjugated Tetracosapentaenoic acid, a conjugated Behenic acid, a conjugated Docosahexaenoic acid, a conjugated Tricosylic acid, a conjugated Lignoceric acid, a conjugated Pentacosylic acid, a conjugated Cerotic acid, a conjugated Heptacosylic acid, a conjugated Montanic acid, a conjugated Nonacosylic acid, a conjugated Melissic acid, a conjugated Henatriacontylic acid, a conjugated Lacceroic acid, a conjugated Psyllic acid, a conjugated Geddic acid, a conjugated Ceroplastic acid, a conjugated Hexatriacontylic acid, or a combination thereof.

54. The composition according to embodiment 53, wherein the conjugated Linoleic acid comprises a cis-9, trans-11, conjugated linoleic acid, cis-9, cis-11, conjugated linoleic acid, trans-9, trans-11, conjugated linoleic acid, and trans-9, cis-11, conjugated linoleic acid, cis-10, trans-12, conjugated linoleic acid, cis-10, cis-12, conjugated linoleic acid, trans-10, trans-12, conjugated linoleic acid, and trans-10, cis-12, conjugated linoleic acid, or any combination thereof.

55. The composition according to embodiment 49 or 50, wherein the fatty acid is an omega-3 fatty acid, an omega-6 fatty acid, an omega-7 fatty acid, an omega-9 fatty acid, or any combination thereof.

56. The composition according to embodiment 55, wherein the omega-3 fatty acid is Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (Clupanodonic acid) (22:5), Docosahexaenoic acid (22:6), Tetracosapentaenoic acid (24:5), Tetracosahexaenoic acid (Nisinic acid) (24:6), or any combination thereof.

57. The composition according to embodiment 55 or 56, wherein the omega-6 fatty acid is Linoleic acid (18:2), γ-linolenic acid (18:3), Calendic acid (18:3), Eicosadienoic acid (20:2), Dihomo-γ-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5), or any combination thereof.

58. The composition according to any one of embodiments 55-57, wherein the omega-7 fatty acid is 5-Dodecenoic acid, 7-Tetradecenoic acid, 9-Hexadecenoic acid (Palmitoleic acid), 11-Decenoic acid (Vaccenic acid), 13-Eicosenoic acid (Paullinic acid), 15-Docosenoic acid, 17-Tetracosenoic acid, and 9Z,11E conjugated Linoleic acid (Rumenic acid), or any combination thereof.

59. The composition according to any one of embodiments 55-58, wherein the omega-9 fatty acid Oleic acid, Elaidic acid, Eicosenoic acid, Mead acid, Erucic acid, Nervonic acid, and Ricinoleic acid, or any combination thereof.

60. The composition according to any one of embodiments 1-48, wherein the composition includes a benzo(iso)oxazolepiperidine and a 5α reductase inhibitor.
61. The composition according to embodiment 60, wherein the benzo(iso)oxazolepiperidine is an optionally substituted Iloperidone, an optionally substituted ocaperidone, an optionally substituted paliperidone, an optionally substituted risperidone, or any combination thereof.
62. The composition according to embodiment 60 or 61, wherein the 5α reductase inhibitor is Alfatradiol, Bexlosteride, Dutasteride, Epristeride, Finasteride, Isotretinoin, Lapisteride, Turosteride, or any combination thereof.
63. The composition according to any one of embodiments 1-48, wherein the composition includes a benzo(iso)oxazolepiperidine and a chemotherapeutic agent or an anti-proliferative agent.
64. The composition according to embodiment 63, wherein the benzo(iso)oxazolepiperidine is an optionally substituted Iloperidone, an optionally substituted ocaperidone, an optionally substituted paliperidone, an optionally substituted risperidone, or any combination thereof.
65. The composition according to embodiment 63 or 64, wherein the chemotherapeutic agent or anti-proliferative agent is an alkylating agent, a platinum agent, an antimetabolite, a topoisomerase inhibitor, an antitumor antibiotic, an aromatase inhibitor, a thymidylate synthase inhibitor, a DNA antagonist, farnesyltransferase inhibitor, a pump inhibitor, a histone acetyltransferase inhibitor, a metalloproteinase inhibitor, a ribonucleoside reductase inhibitor, a TNFα agonist, a TNFα antagonist, an endothelin A receptor antagonist, a retinoic acid receptor agonist, an immuno-modulator, a hormonal and antihormonal agent, a photodynamic agent, a tyrosine kinase inhibitor, or any combination thereof.
66. A method of treating an individual with a disorder associated with androgen production, the method comprises the step of administering to an individual in need thereof a pharmaceutical composition as defined in embodiments 1-65, wherein administration reduces a symptom of a disorder associated with androgen production, thereby treating the individual.
67. The method according to embodiment 66, wherein administration of the pharmaceutical composition reduces the occurrence of an unwanted side.
68. The method according to embodiment 67, wherein the unwanted side includes feminization in males or defeminisation of females.
69. The method according to any one of embodiments 66-68, wherein the symptom is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
70. The method according to any one of embodiments 66-69, wherein the symptom includes the frequency of a symptom, the number of symptoms, the severity of a symptom, or any combination thereof.
71. The method according to any one of embodiments 66-70, wherein the therapeutically effective amount of the therapeutic compound is in the range of about 0.01 mg/kg/day to about 50 mg/kg/day.
72. The method according to any one of embodiments 66-71, wherein the therapeutically effective amount of the therapeutic compound is in the range of about 1 mg/day to about 500 mg/day.
73. The method according to any one of embodiments 66-72, wherein the therapeutically effective amount of the therapeutic compound is in the range of about 1 µM/day to about 1,000 µM/day.
74. The method according to any one of embodiments 66-73, wherein the disorder associated with androgen production.
75. The method according to embodiment 74, wherein the disorder associated with androgen production is a disorder associated with steroid hydroxy-dehydrogenase activity, a disorder associated with HSD17B activity, a disorder associated with HSD17B10 activity, or any combination thereof.
76. The method according to embodiment 74, wherein the disorder associated with androgen production is a hormone-dependent disorder.
77. The method according to embodiment 76, wherein the hormone-dependent disorder is a hormone-dependent proliferative disorder.
78. The method according to embodiments 76, wherein the hormone-dependent disorder is a hormone-dependent non-proliferative disorder.
79. The method according to embodiments 76, wherein the hormone-dependent disorder is a cancer.
80. The method according to embodiment 68, wherein the cancer is a prostate cancer, a lung cancer, a breast cancer, an ovarian cancer, testicular cancer, an adenocarcinoma, a neuroendocrine cancer, or a pancreatic cancer.
81. The method according to embodiment 79, wherein the cancer is an adenocarcinoma.
82. The method according to embodiment 81, wherein the adenocarcinoma is an esophageal cancer, a pancreatic cancer, a prostate cancer, a cervical cancer, a stomach cancer, a throat cancer, a non-small cell lung cancer, a ductal carcinoma of the breast including invasive ductal carcinoma and ductal carcinoma in situ, a lobular carcinoma of the breast including an invasive lobular carcinoma, a colorectal cancer, an adenocarcinoma of the lung including large cell lung cancer, squamous cell lung cancer, small-cell lung cancer, bronchioloalveolar lung cancer, and non-small cell lung cancer, a cholangiocarcinoma or a vaginal cancer.
83. The method according to embodiment 82, wherein the lung cancer is a non-small cell lung cancer.
84. The method according to embodiment 79, wherein the cancer is a hormone-refractory cancer.
85. The method according to embodiments 76, wherein the hormone-dependent disorder is benign prostatic hyperplasia (BPH) or polycystic ovary syndrome.
86. The method according to embodiments 76, wherein the hormone-dependent disorder is acne vulgaris, seborrhea, or female hirsutism.
87. The method according to embodiments 76, wherein the hormone-dependent disorder is androgenic alopecia.
88. Use of a pharmaceutical composition as defined in embodiments 1-65 for the manufacture of a medicament for the treatment of a disorder associated with androgen production.
89. Use of a pharmaceutical composition as defined in embodiments 1-65 for treating a disorder associated with androgen production.
90. The use according to embodiment 88 or 89, wherein administration of the pharmaceutical composition reduces the occurrence of an unwanted side.
91. The use according to embodiment 90, wherein the unwanted side includes feminization in males or defeminisation of females.

92. The use according to any one of embodiments 88-91, wherein the symptom is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.
93. The use according to any one of embodiments 88-92, wherein the symptom includes the frequency of a symptom, the number of symptoms, the severity of a symptom, or any combination thereof.
94. The use according to any one of embodiments 88-93, wherein the amount of the therapeutic compound administered is in the range of about 0.01 mg/kg/day to about 50 mg/kg/day.
95. The use according to any one of embodiments 88-93, wherein the amount of the therapeutic compound administered is in the range of about 1 mg/day to about 500 mg/day.
96. The use according to any one of embodiments 88-93, wherein the amount of the therapeutic compound administered is in the range of about 1 µM/day to about 1,000 µM/day.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods or uses of treating a disorder disclosed herein.

Example 1

HSD10 Enzyme Inhibition Assay

An HSD10 inhibition assay was performed to determine the effect of several anti-psychotics on enzyme activity.

PC3 cells are from a cell line derived from a hormone refractory prostate cancer and are known to overexpress HSD10. PC3 cells were seeded at a density of 4,000 cells per well in a 96 well plate, and incubated at 37° C., 5% $CO_2$ for 48 hours in standard growth media (F12K nutrient media, 7% Fetal Calf Serum, 2 mM L-Glutamine, 45 mg/L ascorbic acid). The media was then removed by pipette and replaced with the appropriate drug treatment as follows: 50 µM Chlorpromazine (a typical anti-psychotic) in PC3 treatment media (F12K nutrient media, 125 µM fatty acid free BSA, 2 mM L-Glutamine, 45 mg/L ascorbic acid); 50 µM Clozapine (an atypical anti-psychotic) in PC3 treatment media; 50 µM Clomipramine (a tricyclic anti-depressant) in PC3 treatment media; 50 µM Risperidone (an atypical anti-psychotic) in PC3 treatment media; 50 µM Diphenhydramine (a sedative) in PC3 treatment media. Cells line tests were carried out in presence and absence of testosterone for comparison. After incubation in the drug treatment for 96 hours at 37° C., 5% $CO_2$, the supernatant was removed from all wells of cells, and cells washed with 200 µL PBS.

After removal of the PBS, cell number was determined using a lysed cell LDH assay (CytoTox 96 Non-radioactive cytotoxicity assay (LDH Assay); Promega, Co., Madison Wis.). Cells were lysed with 0.9% Triton-X in PBS for 2 hours at 37° C., 5% $CO_2$ and 50 µL of this cell lysate was transferred to a fresh 96 well plate. About 50 µL of CytoTox 96 assay reagent was added to the transferred cell lysate and this mixture was incubated at room temperature in the dark for 20 minutes. After the addition of 50 µL stop reagent, the optical absorbance was determined for each incubated mixture at 492 nm. The percentage cell number was calculated by normalizing the experimental counts, where 100% is set to cells receiving no drug treatment, and 0% is set to readings from wells containing no cells. The mean and standard error was calculated from at least 3 wells.

As seen in Table 1, Risperidone showed an inhibitory effect on both oxidative (88% inhibition) and reductive (63% inhibition) performance of HSD10. No other drug tested appeared to have effectively inhibited both oxidative and reductive performance of HSD10.

TABLE 1

HSD10 Enzymatic Activity in Presence of Different Drugs

| Drug | Oxidative Activity | | Reductive Activity | |
|---|---|---|---|---|
| | Rate (µM/min) | Drug Inhibition | Rate (µM/min) | Drug Inhibition |
| No Drug | 8.4 | 0% | 8.8 | 0% |
| Chlorpromazine | 7.7 | 8% | 7.2 | 18% |
| Clozapine | 4.8 | 43% | 7.5 | 15% |
| Clomipramine | 2.3 | 73% | 7.5 | 15% |
| Risperidone | 1.0 | 88% | 3.3 | 63% |
| Diphenhydramine | 8.0 | 5% | 8.3 | 6% |

A cell metabolism inhibition assay was performed to determine the effect of different fatty acids on cellular metabolic rate. The fatty acids tested were α-Linolenic acid, omega 3 fatty acid (ALA), Arachidonic acid, omega 6 fatty acid (AA), 9Z,11E conjugated Linoleic acid, omega 7 fatty acid (CLA), Docosahexaenoic acid, omega 3 fatty acid (DHA), Eicosapentaenoic acid, omega 3 fatty acid (EPA), Oleic acid, omega 9 fatty acid (OA), Ricinoleic acid, omega 9 hydroxylated fatty acid (RA).

PC3 cells are from a cell line derived from a hormone refractory prostate cancer and are known to overexpress HSD10. PC3 cells were seeded at a density of 4,000 cells per well in a 96 well plate, and incubated at 37° C., 5% $CO_2$ for 48 hours in standard growth media (F12K nutrient media, 7% Fetal Calf Serum, 2 mM L-Glutamine, 45 mg/L ascorbic acid). The media was then removed by pipette and replaced with the appropriate drug treatment as follows: 20 µM, or 40 µM, or 60 µM, or 80 µM, or 100 µM ALA in PC3 treatment media (F12K nutrient media, 125 uM fatty acid free BSA, 2 mM L-Glutamine, 45 mg/L ascorbic acid); 20 µM, or 40 µM, or 60 µM, or 80 µM, or 100 µM AA in PC3 treatment media; 20 µM, or 40 µM, or 60 µM, or 80 µM, or 100 µM CLA in PC3 treatment media; 20 µM, or 40 µM, or 60 µM, or 80 µM, or 100 µM DHA in PC3 treatment media; 20 µM, or 40 µM, or 60 µM, or 80 µM, or 100 µM EPA in PC3 treatment media; 20 µM, or 40 µM, or 60 µM, or 80 µM, or 100 µM OA in PC3 treatment media; and 20 µM, or 40 µM, or 60 µM, or 80 µM, or 100 µM RA in PC3 treatment media. After incubation in the drug treatment for 72 hours at 37° C., 5% $CO_2$, 50 µL Cell titre Blue Assay Reagent was added to each well and the plate return to incubation at 37° C., 5% $CO_2$, for a further 24 hours, at which time the absorbance at 620 nm was recorded. The reduction of absorbance at 620 nm represents a higher metabolic rate, and the data below has been normalized such that 100% represents cells that have been grown in the presence of undrugged media, and 0% represents wells containing no cells.

As seen in Table 2, AA, CLA, DHA, and EPA showed a significant inhibitory effect on cellular metabolic activity. AA showed about 35-40% metabolic inhibition in the 80-100 μM range. CLA showed at least about 35-40% metabolic inhibition in the 60-100 μM range. DHA showed about 40-65% metabolic inhibition in the 60-100 μM range. EPA showed about 50-65% metabolic inhibition in the 80-100 μM range.

TABLE 2

Cellular Metabolic Activity in Presence of Different Fatty Acids

| Fatty Acid | 20 μM | 40 μM | 60 μM | 80 μM | 100 μM |
|---|---|---|---|---|---|
| ALA | 118 ± 0.5 | 118 ± 0.9 | 118 ± 0.2 | 117 ± 0.9 | 114 ± 1.2 |
| AA  | 107 ± 3.9 | 90 ± 5.6  | 78 ± 6.4  | 66 ± 7.2  | 60 ± 5.9  |
| CLA | 86 ± 2.4  | 71 ± 3.8  | 59 ± 2.8  | 63 ± 4.0  | 67 ± 5.0  |
| DHA | 90 ± 8.2  | 74 ± 7.6  | 58 ± 5.9  | 49 ± 7.7  | 34 ± 7.0  |
| EPA | 94 ± 9.4  | 71 ± 8.2  | 67 ± 7.4  | 49 ± 7.4  | 37 ± 5.9  |
| OA  | 109 ± 2.7 | 108 ± 0.9 | 111 ± 2.2 | 110 ± 2.2 | 111 ± 2.0 |
| RA  | 91 ± 6.0  | 94 ± 4.7  | 90 ± 6.2  | 90 ± 6.0  | 94 ± 3.1  |

Example 2

Cell Growth Inhibition Assay

To determine whether Risperidone could be effective in inhibiting growth of cancer cells overexpressing HSD10, a lysed cell LDH assay was conducted using cells from a PC3 cell line.

PC3 cells are from a cell line derived from a hormone refractory prostate cancer and are known to overexpress HSD10. PC3 cells were seeded at a density of 4,000 cells per well in a 96 well plate, and incubated at 37° C., 5% $CO_2$ for 48 hours in standard growth media (F12K nutrient media, 7% Fetal Calf Serum, 2 mM L-Glutamine, 45 mg/L ascorbic acid). The media was then removed by pipette and replaced with the appropriate drug treatment as follows: 12.5 μM, 25 μM, or 50 μM Risperidone in PC3 treatment media (F12K nutrient media, 125 uM fatty acid free BSA, 2 mM L-Glutamine, 45 mg/L ascorbic acid); 12.5 μM, 25 μM, or 50 μM CLA in PC3 treatment media; 12.5 μM, 25 μM, or 50 μM DHA in PC3 treatment media; 12.5 μM Risperidone and 12.5 μM CLA, DHA, or both CLA and DHA in PC3 treatment media; 25 μM Risperidone and 25 μM CLA, DHA, or both CLA and DHA in PC3 treatment media; and 50 μM Risperidone and 50 μM CLA, DHA, or both CLA and DHA in PC3 treatment media. Cells line tests were carried out in presence and absence of testosterone for comparison. After incubation in the drug treatment for 96 hours at 37° C., 5% $CO_2$, the supernatant was removed from all wells of cells, and cells washed with 200 μL PBS.

After removal of the PBS, cell number was determined using a lysed cell LDH assay (CytoTox 96 Non-radioactive cytotoxicity assay (LDH Assay); Promega, Co., Madison Wis.). Cells were lysed with 0.9% Triton-X in PBS for 2 hours at 37° C., 5% $CO_2$ and 50 μL of this cell lysate was transferred to a fresh 96 well plate. About 50 μL of CytoTox 96 assay reagent was added to the transferred cell lysate and this mixture was incubated at room temperature in the dark for 20 minutes. After the addition of 50 μL stop reagent, the optical absorbance was determined for each incubated mixture at 492 nm. The percentage cell number was calculated by normalizing the experimental counts, where 100% is set to cells receiving no drug treatment, and 0% is set to readings from wells containing no cells. The mean and standard error was calculated from at least 3 wells.

The results show that 50 μM Risperidone exhibited about 50% growth inhibition of PC3 cells (Table 3). In addition, although having no effect alone, CLA in combination Risperidone had a synergistic effect, inhibiting PC3 cell growth by over 60%.

TABLE 3

Anti-Cancer Activity of Risperidone in PC3 Cells

| | Percentage of Lysed Cells (%) | | | | | |
|---|---|---|---|---|---|---|
| Concentration | Risperidone | Risperidone plus CLA | Risperidone plus DHA | Risperidone plus DHA/CLA | CLA | DHA |
| 12.5 μM | 102 ± 5.4  | 104 ± 3.2 | 114 ± 5.5 | 113 ± 1.6  | 109 ± 0.56 | 109 ± 1.1 |
| 25 μM   | 93 ± 0.51  | 85 ± 1.7  | 102 ± 0.12| 88 ± 1.9   | 112 ± 1.1  | 102 ± 3.5 |
| 50 μM   | 52 ± 0.22  | 38 ± 1.8  | 66 ± 3.4  | 36 ± 0.47  | 107 ± 2.4  | 95 ± 3.8  |

To determine the optimal concentration of Risperidone and CLA necessary to inhibit cell growth, a lysed cell LDH assay was conducted using various concentration of Risperidone and CLA. PC3 cells were cultured and a lysed cell LDH assay was conducted as described above, except that the various drug treatments evaluated contained either 0 μM, 12.5 μM, 25 μM, or 50 μM Risperidone in combination with 0 μM, 6.25 μM, 12.5 μM, 25 μM, 50 μM, or 100 μM CLA (see Table 3).

The data demonstrated that combination treatments comprising 50 μM Risperidone and either 50 or 100 μM CLA exhibited about 65% growth inhibition of PC3 cells (Table 4). In addition, 50 μM Risperidone and 25 μM CLA or 25 μM Risperidone and 50 μM CLA both exhibited about 50% growth inhibition of PC3 cells (Table 4). These inhibitory effects were all synergistic in nature since treatment containing either 25 μM or 50 μM Risperidone alone only inhibited cell growth by about 20-30%.

TABLE 4

Anti-Cancer Activity of Risperidone and CLA Combinations in PC3 Cells

| Risperidone Concentration | Percentage of Lysed Cells (%) CLA Concentration | | | | | |
|---|---|---|---|---|---|---|
| | 0 µM | 6.25 µM | 12.5 µM | 25 µM | 50 µM | 100 µM |
| 0 µM | 100 | 96 ± 0.7 | 90 ± 2.7 | 112 ± 9.5 | 103 ± 9.3 | 66 ± 11.8 |
| 12.5 µM | 81 ± 3.6 | 114 ± .2.2 | 112 ± 7.1 | 95 ± 2.5 | — | — |
| 25 µM | 73 ± 2.2 | — | 94 ± 1.8 | 89 ± 6.8 | 54 ± 2.8 | — |
| 50 µM | 79 ± 0.7 | — | — | 55 ± 2.6 | 36 ± 0.81 | 34 ± 1.2 |

Example 3

Cell Growth Inhibition Assay

To determine whether Risperidone could be effective in inhibiting growth of cancer cells overexpressing HSD10, a lysed cell LDH assay was conducted using cells taken from a prostate cancer cell line, a lung cancer cell line, a breast cancer cell line, an ovarian cancer cell line, each of which was known to overexpress HSD10, and a non-cancerous cell line.

To determine whether Risperidone alone, or in combination with CLA could inhibit cell growth of cells taken from a prostate cancer cell line overexpressing HSD10, a lysed cell LDH assay was conducted on PC3 cells as described in Example 2, except that the various drug treatments evaluated contained: 50 µM Risperidone in PC3 treatment media; 50 µM CLA in PC3 treatment media; 50 µM Risperidone and 50 µM CLA in PC3 treatment media; 50 µM Risperidone and 1 µM Testosterone (T) in PC3 treatment media; 50 µM Risperidone, 50 µM CLA, and 1 µM Testosterone in PC3 treatment media.

To determine whether Risperidone alone, or in combination with CLA could inhibit cell growth of cells taken from a lung cancer cell line overexpressing HSD10, A549 cells were seeded at a density of 2,000 cells per well in a 96 well plate, and incubated at 37° C., 5% $CO_2$ for 48 hours in standard growth media (DMEM nutrient media, 10% Fetal Calf Serum, 2 mM L-Glutamine). The media was then removed by pipette and replaced with the appropriate drug treatment as follows: 50 µM Risperidone in A459 treatment media (DMEM nutrient media, 125 uM fatty acid free BSA, 2 mM L-Glutamine); 50 µM CLA in A459 treatment media; 50 µM Risperidone and 50 µM CLA in A459 treatment media; 50 µM Risperidone and 1 µM Testosterone in A459 treatment media; 50 µM Risperidone, 50 µM CLA, and 1 µM Testosterone in A459 treatment media. After incubation in the drug treatment for 96 hours at 37° C., 5% $CO_2$, the supernatant was removed from all wells of cells, and cells washed with 200 µL PBS.

To determine whether Risperidone alone, or in combination with CLA could inhibit cell growth of cells taken from a breast cancer cell line overexpressing HSD10, MCF7 cells were seeded at a density of 4,000 cells per well in a 96 well plate, and incubated at 37° C., 5% $CO_2$ for 48 hours in standard growth media (EMEM nutrient media, 10% Fetal Calf Serum, 2 mM L-Glutamine, 0.1 mM non-essential amino acids). The media was then removed by pipette and replaced with the appropriate drug treatment as follows: 50 µM Risperidone in MCF7 treatment media (EMEM nutrient media, 125 uM fatty acid free BSA, 2 mM L-Glutamine, 0.1 mM non-essential amino acids); 50 µM CLA in MCF7 treatment media; 50 µM Risperidone and 50 µM CLA in MCF7 treatment media; 50 µM Risperidone and 1 µM Testosterone in MCF7 treatment media; 50 µM Risperidone, 50 µM CLA, and 1 µM Testosterone in MCF7 treatment media. After incubation in the drug treatment for 96 hours at 37° C., 5% $CO_2$, the supernatant was removed from all wells of cells, and cells washed with 200 µL PBS.

To determine whether Risperidone alone, or in combination with CLA could inhibit cell growth of cells taken from an ovarian cancer cell line overexpressing HSD10, OVCAR-3 cells were seeded at a density of 8,000 cells per well in a 96 well plate, and incubated at 37° C., 5% $CO_2$ for 48 hours in standard growth media (RPMI-1640 nutrient media, 20% Fetal Calf Serum, 2 mM L-Glutamine, 0.01 mg/mL insulin, 4.5 g/L glucose, 10 mM HEPES, 1 mM sodium pyruvate). The media was then removed by pipette and replaced with the appropriate drug treatment as follows: 50 µM Risperidone in OVCAR-3 treatment media (RPMI-1640 nutrient media, 0.5% Fetal Calf Serum, 125 uM fatty acid free BSA, 2 mM L-Glutamine, 0.01 mg/mL insulin, 4.5 g/L glucose, 10 mM HEPES, 1 mM sodium pyruvate); 50 µM CLA in OVCAR-3 treatment media; 50 µM Risperidone and 50 µM CLA in OVCAR-3 treatment media; 50 µM Risperidone and 1 µM Testosterone in OVCAR-3 treatment media; 50 µM Risperidone, 50 µM CLA, and 1 µM Testosterone in OVCAR-3 treatment media. After incubation in the drug treatment for 96 hours at 37° C., 5% $CO_2$, the supernatant was removed from all wells of cells, and cells washed with 200 µL PBS.

To determine whether Risperidone alone, or in combination with CLA could inhibit cell growth of cells taken from a non-cancerous cell line, VERO cells, derived from kidney cells) were seeded at a density of 2,000 cells per well in a 96 well plate, and incubated at 37° C., 5% $CO_2$ for 48 hours in standard growth media (EMEM nutrient media, 10% Fetal Calf Serum, 2 mM L-Glutamine, 1 mM sodium pyruvate). The media was then removed by pipette and replaced with the appropriate drug treatment as follows: 50 µM Risperidone in VERO treatment media (EMEM nutrient media, 125 uM fatty acid free BSA, 2 mM L-Glutamine, 1 mM sodium pyruvate); 50 µM CLA in VERO treatment media; 50 µM Risperidone and 50 µM CLA in VERO treatment media; 50 µM Risperidone and 1 µM Testosterone in VERO treatment media; 50 µM Risperidone, 50 µM CLA, and 1 µM Testosterone in VERO treatment media. After incubation in the drug treatment for 96 hours at 37° C., 5% $CO_2$, the supernatant was removed from all wells of cells, and cells washed with 200 µL PBS.

After removal of the PBS from the cell cultures described above, cell number was determined using a lysed cell LDH assay. Cells were lysed with 0.9% Triton-X in PBS for 2 hours at 37° C., 5% $CO_2$ and 50 µL of this cell lysate was transferred to a fresh 96 well plate. About 50 µL of CytoTox 96 assay reagent was added to the transferred cell lysate and this mixture was incubated at room temperature in the dark for 20 minutes. After the addition of 50 µL stop reagent, the optical absorbance was determined for each incubated mixture at 492 nm. The percentage cell number was calculated by normalizing the experimental counts, where 100% is set to cells receiving no drug treatment, and 0% is set to readings from wells containing no cells. The mean and standard error was calculated from at least 3 wells.

The results show that 50 µM Risperidone exhibited about 50% growth inhibition of PC3 cells, over 60% growth inhibition of A549 cells, about 65% growth inhibition of MCF7 cells, and about 35% growth inhibition of OVCAR-3 cells (Table 3). In addition, CLA in combination Risperidone demonstrated a synergistic growth inhibition effect on most cancer cell lines tested. Thus, 50 µM Risperidone in combination with CLA exhibited over 60% growth inhibition of PC3 cells, almost 100% growth inhibition of A549 cells, and over 70% growth inhibition of MCF7 cells (Table 3). Importantly, neither Risperidone nor CLA had any measurable effect on growth on cell from the non-cancerous cell line VERO.

The results also show that the mechanism of action of Resperidone is related to Testosterone in that adding an external source of Testosterone to Risperidone-treated cells partially negated the effect of the Risperidone alone. However, in the presence of CLA, Testosterone failed to negate the effect of the Risperidone. This suggests the CLA is acting on one Testosterone pathway and Risperidone on another Testosterone pathway. None of the cells from the cell lines tested responded to a 1 µM Testosterone treatment without drug present.

TABLE 5

Anti-Cancer Activity of Risperidone in Various Cancer Cells

Percentage of Lysed Cells (%)

| Cell Line | Risperidone | CLA | Risperidone plus CLA | Risperidone plus T | Risperidone plus CLA/T |
|---|---|---|---|---|---|
| PC3 | 52 ± 1.7 | 107 ± 2.4 | 38 ± 1.8 | 67 ± 2.8 | 41 ± 4.3 |
| A549 | 38 ± 1.9 | 4.5 ± 0.3 | 1 ± 0.1 | 48 ± 4.1 | 1 ± 0.1 |
| MCF7 | 35 ± 2.4 | 56 ± 2.6 | 28 ± 0.6 | 54 ± 3.6 | 26 ± 1.1 |
| OVCAR-3 | 64 ± 0.4 | 87 ± 6.0 | 69 ± 2.1 | 84 ± 4.0 | 70 ± 1.8 |
| VERO | 94 ± 1.7 | 98 ± 2.7 | 94 ± 3.5 | 96 ± 0.9 | 98 ± 1.8 |

Example 4

Cell Growth Inhibition Assay

To determine whether Risperidone alone, or in combination with CLA could inhibit cell growth of cells taken from a pancreatic cancer cell line overexpressing HSD10, a resazurin-based cell viability assay was conducted on Bx-PC3 cells.

BxPC-3 cells are from a cell line derived from a human pancreatic adenocarcinoma and are known to overexpress HSD10. BxPC-3 cells were seeded at a density of 4,000 cells per well in a 384 well plate, and incubated at 37° C., 5% $CO_2$ for 24 hours in standard growth media (RPMI nutrient media, 5% heat-inactivated Fetal Calf Serum, 2 mM L-Glutamine). The media was then removed by pipette and replaced with 50 µL BxPC-3 treatment media comprising 125 µM fatty acid-free BSA, 2 mM L-Glutamine and one of the following drug treatments: 0.1 µM, 2 µM, or 50 µM Risperidone; 0.1 µM, 2 µM, or 50 µM CLA; or 0.1 µM, 2 µM, or 50 µM of Risperidone and CLA (in equimolar amounts). After incubation in the drug treatment for 72 hours at 37° C., 5% $CO_2$, viable cell number was determined using a resazurin-based cell viability assay (PRESTO-BLUE®; Invitrogen, Carlsbad, Calif.). To each well, 7 µL of PRESTOBLUE® reagent was added and the plates incubated for 60 minutes at 37° C., 5% $CO_2$. After incubation, the fluorescence intensity of each well was determined using a microplate reader by excitation and 570 nm and recording emission at 600 nm. The percentage of viable cell number was calculated by normalizing the experimental fluorescence intensity, where 100% is set to cells receiving no drug treatment (cells metabolizing at optimal rate), and 0% is set to readings from cells treated with Paclitaxel (cells not metabolizing at all due to their destruction by anti-cancer drug). A value under 50% could be considered a useful indication of potential efficacy.

TABLE 6

Anti-Cancer Activity of Risperidone in Pancreatic Cancer Cells

| Drug Treatment | 0.1 uM | 2 uM | 50 uM |
|---|---|---|---|
| Risperidone | 94% | 85% | 40% |
| CLA | 103% | 71% | 119% |
| Risperidone:CLA | 83% | 50% | 16% |

The results show that Risperidone alone inhibited cancer cell growth, exhibited about 60% growth inhibition of Bx-PC3 cells at 50 µM (Table 6). Surprisingly, although having no effect cytostatic or cytotoxic alone, CLA, in combination Risperidone, had a synergistic effect, with equimolar combinations inhibiting Bx-PC3 cell growth by about 50% at 2 uM and about 84% at 50 uM.

Example 5

In Vivo Animal Model Studies on Prostate Cancer

In vivo studies were performed to determine the effect of Risperidone in combination with Rumenic acid on orthotopic prostate tumor growth in a mouse xenograft model utilizing novel luciferase labelled BxPC-3 cells. Immunodeficeint male mice (athymic nude mice) were acclimated to the laboratory for at least one week prior to implantation of tumor. PC-3M-luc cells obtained directly from in vitro culture were then injected into the prostate on Day 0. Animals were divided into six groups of 12 mice each. Primary tumor size and metastases were assessed by bioluminescence measurements on day 6, 13, 20, 27, 34, and 40. On day 7 a five week treatment regime was initiated. Both individual drug and high and low dose combination were examined by administering the drugs twice daily on an individual body weight basis using a dose escalation protocol (Table 7). If tumors grew above a pre-determined level, or mice lost more than 10% of bodyweight, they were culled. The primary tumor was excised, weighed and measured. Individual organs were imaged to assess metastatic burden.

TABLE 7

Dosing Regime of Animal Groups

| Day | Animal Group | | | | | |
|---|---|---|---|---|---|---|
| | 1 Vehicle | 2 Risperidone | 3 Rumenic Acid | 4 Low Dose Combination* | 5 High Dose Combination* | 6 Docetaxel |
| 7 | — | 0.25 mg/kg oral BID | 0.18 mg/kg oral BID | 0.25 mg/kg 1:1 combination oral BID | 0.25 mg/kg 1:1 combination oral BID | 5 mg/kg i.v. twice weekly, plus BID oral vehicle (as Group 1) |
| 11 | — | 0.5 mg/kg oral BID | 0.35 mg/kg oral BID | 0.5 mg/kg 1:1 combination oral BID | 0.5 mg/kg 1:1 combination oral BID | 5 mg/kg i.v. twice weekly, plus BID oral vehicle (as Group 1) |
| 15 | — | 1.0 mg/kg oral BID | 0.70 mg/kg oral BID | 0.5 mg/kg 1:1 combination oral BID | 1.0 mg/kg 1:1 combination oral BID | 5 mg/kg i.v. twice weekly, plus BID oral vehicle (as Group 1) |

*combination doses were calculated according to the dosage of Risperidone; rumenic acid was added to an equimolar level.

One parameter of increased efficacy measured was animal survival in each group, both in terms of overall survival at the end of the study as well as survival rate. Group 1 animals were dosed on a vehicle and served as the negative control and exhibited an overall survivorship of 45% (Table 8). Group 6 animals were dosed on Docetaxel and served as the positive control; this group showed 100% survival at day 40 (Table 8). Looking at the groups where only a single drug was administered, Group 2 (Risperidone) showed an overall survivorship of 33% while Group 3 (Rumenic Acid) showed an overall survivorship of 45% (Table 8). These results indicate that administration of a single drug alone was ineffective in treating prostate cancer. On the other hand, groups where a drug combination was administered revealed increased overall survivorship of animals. Animals from Group 4 and 5 were dosed low and high Risperidone and Rumenic Acid combinations. Group 4 animals showed an overall survivorship of 70% while Group 5 animals showed an overall survivorship of 64% (Table 8). These results demonstrate a synergistic interaction between Risperidone and Rumenic Acid as neither drug alone was effective, yet in combination these drugs increased overall survival by at least 1.4-fold and as much as 2.1-fold. Thus, both the low and high dose drug combinations exhibited increase efficacy by improving overall survivorship in the treated animals.

TABLE 8

Dosing Regime of Animal Groups

| Group | Animal Survival | Tumor Growth Inhibition* |
|---|---|---|
| 1 | 45% | 0% |
| 2 | 33% | 16% |
| 3 | 45% | 21% |
| 4 | 70% | 70% |
| 5 | 64% | 65% |
| 6 | 100% | 94% |

*Tumor growth inhibition data is as calculated on Day 34, except for Group 5 which had sufficient mice alive to calculate on Day 40.

Figure 2:
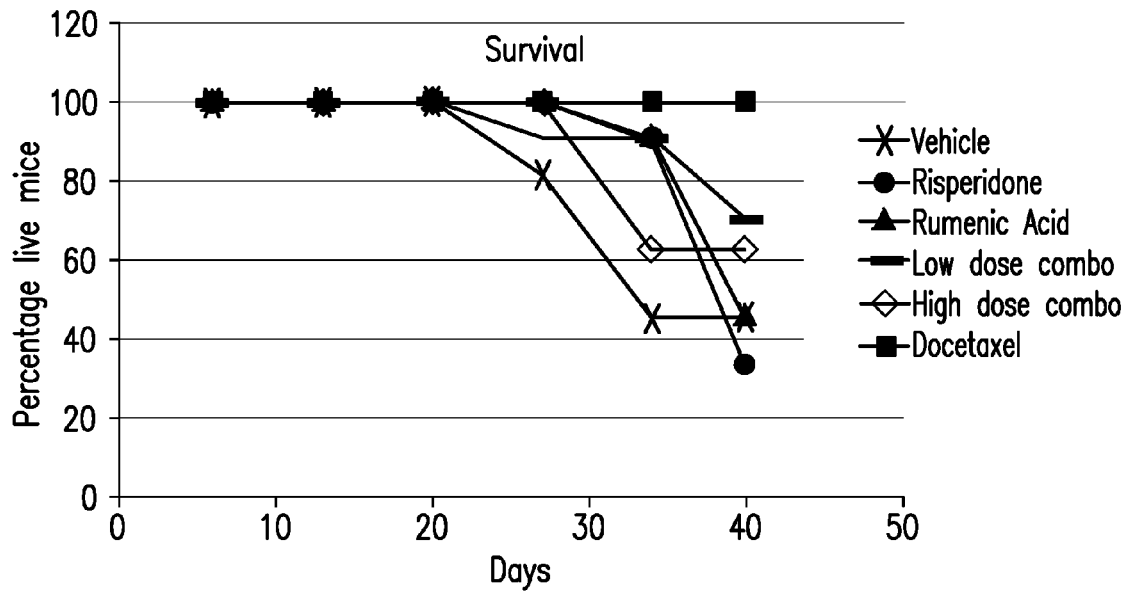
FIG. 2 shows the survival rate of animal groups treated with different drug and drug combinations.

With regards to survival rate, a decline in the survival of Group 1 (Vehicle) animals was observed by day 27 with an almost 20% animal loss and continued to drop steadily throughout the course of the study (FIG. 2). Group 6 (Docetaxel) animals showed 100% survival throughout the course of the study (FIG. 2). Similar to overall survivorship, animals belonging to the groups where only a single drug was administered showed no real differences when compared to Group 1 animals (negative control). For example, animals from Group 2 (Risperidone) showed an onset delay of tumor lethality as a decrease in survivorship rate was pushed back to day 34 with only about 10% animal loss. However, a rapid decrease of survive rate was then observed resulting in only 33% animal survivorship by day 40 (FIG. 2). Similarly, animals from Group 3 (Rumenic Acid) showed a decline in the survival rate by day 27. Although survival remained high with only about 10% animal loss by day 34, there was a sharp decline in survival rates until only 45% of the mice were alive by day 40 (FIG. 2). In contrast, both the onset of tumor lethality and the survival rate improved in animals treated with the combination therapy. For example, a decline in survival rate was not observed until day 34 with about 10% (Group 5) or 34% (Group 4) loss of animals (FIG. 2). By day 40, 70% of the animals in Group 4 were alive whereas 64% of the animals in Group 5 were also alive (FIG. 2). These results demonstrate that both the low and high dose drug combinations showed increase efficacy by increasing survival rates both in terms of delaying the onset of tumor lethality and well as improving the survival rate in the treated animals.

Figure 3:
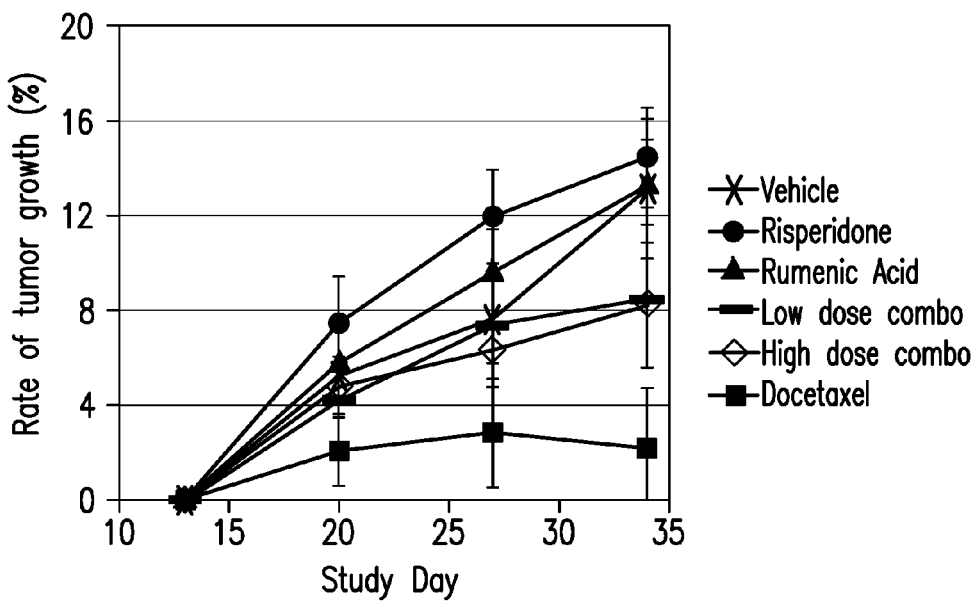
FIG. 3 shows the tumor growth inhibition rate of animal groups treated with different drug and drug combinations.

Another parameter of increased efficacy measured was growth inhibition of the prostate tumor. Group 1 (Vehicle) animals severing as the negative control showed no inhibition of tumor growth, whereas Group 6 (Docetaxel) animals severing as the positive control showed a 94% inhibition of tumor growth (Table 8). Animal groups treated with a single drug regime showed little effect on tumor growth inhibition. Animals from Group 2 (Risperidone) showed only a 16% inhibition of tumor growth (Table 8). Similarly, Group 3 (Rumenic Acid) animals showed only a 21% inhibition of tumor growth (Table 8). In contrast, animal groups treated with both low and high dose drug combinations exhibited significant tumor growth inhibition. For example, animals from Group 4 (Low Dose) showed 70% inhibition of tumor growth whereas animals from Group 5 (High Dose) showed 65% inhibition of tumor growth (Table 8). Analysis of tumor growth inhibition throughout the course of the study indicated that the rate of tumor growth inhibition was consistent (FIG. 3). These results demonstrate that both the low and high dose drug combinations showed increase efficacy by dramatically inhibiting tumor growth.

Lastly, the general health and overall condition of the animals in each group was assessed by monitoring body weight throughout the study. Groups 1 (Vehicle) and Group 6 (Docetaxel) animals were on a trend of losing weight by Day 40, whereas Group 4 animals gained weight and Groups 2, 3, 5 animals maintained a constant weight. These results showed that both the low and high dose drug combinations did not adversely affect the general health and overall condition of the animals. In contrast, although demonstrating efficacy, Docetaxel administration had adverse consequences on the general health and overall condition of the animals.

Example 6

In Vivo Animal Model Studies on Pancreatic Cancer

In vivo studies were performed to determine the effect of Risperidone in combination with Rumenic acid on orthotopic pancreatic tumor growth in a mouse xenograft model utilizing novel luciferase labelled BxPC-3 cells. Immunodeficeint male mice (athymic nude mice) were acclimated to the laboratory for at least one week prior to implantation of tumor. BxPC-3 cells obtained directly from in vitro culture were then injected into the pancreas on Day 0. Animals were divided into four groups of 10 mice each which underwent the following treatment regime: Group 1, daily oral administration of vehicle comprising 1% (v/v) ethanol, 20% (v/v) PEG 400, 79% (v/v) acid solution and 0.4% (w/v) TWEEN™ 80 at a final pH of 3.1-3.3 (Control); Group 2, intraperitoneal administration of 60 mg/kg of Reference Compound gemcitabine every third day for four rounds followed by one week rest before repeating the dosing; Group 3, daily oral administration of 1 mg/kg of Test Compound VAL401; and Group 4, daily administration of 2 mg/kg Test Compound VAL401. Administration of Test and Reference Compounds began on Day 1 and continued until Day 33. Body weights of the animals were measured two times a week throughout the in-life phase and blood samples for PK analyses were collected from saphenous vein from all animals 2 hours after compound administration at study Day 24. Primary tumor size and metastases were assessed by bioluminescence measurements on Day 6, 13, 20, 27, and 34 using fluorescent imaging system. The animals were sacrificed at Day 34. At the termination, brain tissues were collected and frozen. Tumors were weighed, measured in three dimensions followed by fixation and embedding in paraffin for possible histopathological assessment. Also spleen, liver and lungs were collected for possible analysis.

Statistical analysis was performed with statistical software R (version 3.1.2). The parameters with multiple measurements in different time points per animal were analyzed using mixed-effects models and model contrasts. The models had fixed effects for treatment, time point, and their interaction. The obtained p-values values were adjusted for multiple comparisons if necessary. The continuous valued end-point parameters were analyzed using parametric or non-parametric test. If the groups were normally distributed with equal variance, parametric one-way ANOVA followed by Tukey's HSD post hoc test was used. If the assumptions were not fulfilled as such or after data transform (e.g. logarithmic), nonparametric Kruskal-Wallis test followed by Mann-Whitney U test was used.

The summary of the results obtained are provided in Table 9. With respect to Group 2, treatment with gemcitabine did not have any effect on animal body weight gain compared to vehicle treatment (Table 9). Animals treated with Gemcitabine did exhibit a statistically significantly decreased pancreatic tumor volume when compared to vehicle group (Table 9). Although not statistically different when compared to vehicle group, Gemcitabine-treated animals also showed a trend in decreased pancreatic tumor weight as well as in the bioluminescence imaging parameters (area, average radiation and total flux) on Day 34 (Table 9).

With respect to Group 3 and 4, treatment VAL401 at either dose did not have any effect on animal body weight gain compared to vehicle treatment (Table 9). Animals treated with VAL401 did exhibited a statistically significant decrease in pancreatic tumor volume in both studied doses and the same trend was seen in pancreatic tumor weight when compared to vehicle group (Table 9). In addition, VAL401-treated animals showed a statistically significant decrease in bioluminescence imaging parameter evaluating area compared to vehicle group on Day 34 and the same trend was seen in in other bioluminescence imaging parameters (average radiation and total flux) (Table 9).

TABLE 9

Summary of Data

| PARAMETER | Gemcitabine | VAL401 dose 1 mg/kg | VAL401 dose 2 mg/kg |
|---|---|---|---|
| Body weight | | | |
| Body weight curves | NS | NS | NS |
| Body weight at sacrifice relative to Day −1 body weight | NS | NS | NS |
| Tumor volume | | | |
| Pancreatic tumor weight | NS | NS | NS |
| Pancreatic tumor volume | ↓** | ↓* | ↓** |
| Bioluminescence imaging | | | |
| Area | NS | NS | NS |
| Average radiation | NS | NS | NS |
| Total flux | NS | NS | NS |
| Area (day 34) | NS | ↓* | ↓* |
| Average radiation (day 34) | NS | NS | NS |
| Total flux (day 34) | NS | NS | NS |

Notation:
*** = statistically significant difference with p-value < 0.001,
** = p-value < 0.01,
* = p-value < 0.05,
a = p-value < 0.1, and
NS = Non-Significant.

Example 7

In Vivo Animal Model Studies on Non-Small Cell Lung Cancer

In vivo studies were performed to determine the effect of Risperidone in combination with Rumenic acid on a subcutaneous non-small cell lung cancer tumor growth in a mouse xenograft model. MF1 female mice were acclimated to the laboratory for at least one week prior to implantation of tumor. H2228 cells obtained directly from in vitro culture were then injected subcutaneously on Day 0. Animals were divided into five groups of 15 mice each which underwent the following treatment regime: Group 1, daily oral administration of vehicle; Group 2, daily oral administration of 50 mg/kg of Reference Compound Crizotinib; Group 3, daily oral administration of 0.1 mg/kg of Test Compound VAL401; and Group 4, daily administration of 0.5 mg/kg Test Compound VAL401; Group 5, daily oral administration of 2 mg/kg of Test Compound VAL401. Administration of Test and Reference Compounds began on Day 22 and continued until Day 64. Body weights of the animals were measured daily throughout the in-life phase and primary tumor size measured with calipers in two dimensions three times a week with volumes calculated using the formula 0.5(L×W×W). The animals were sacrificed at Day 65. At the termination, tumors were weighed, measured in three dimensions.

No significant differences were observed in bodyweight during the experiment. No adverse events were recorded, and no mice were terminated early. Data was assessed such that the treatment groups were pooled and treated mice were observed to be split into 'responder' and 'non-responder' categories. 40% of treated mice responded, and the tumour growth for the groups is seen below in Table 10. The tumour growth of the treatment non-responders is seen to be comparable to the untreated animals, validating the 'non-response' criteria (Table 10). Responders are seen to have significantly lower tumour growth than untreated animals (Table 10).

TABLE 10

Summary of Data

| | Percent Tumour growth (Mean ± Standard Error) | | | |
|---|---|---|---|---|
| | Day 50 | Day 52 | Day 55 | Day 57 |
| Untreated | 31% ± 4.2% | 33% ± 4.3% | 37% ± 4.4% | 40% ± 4.5% |
| Treatment Non-Responders | 31% ± 2.7% | 34% ± 2.9% | 41% ± 3.0% | 46% ± 3.1% |
| Treatment Responders | 17% ± 2.8% | 18% ± 2.5% | 19% ± 2.3% | 19% ± 2.0% |

Example 8

Treatment of a Disorder Associated with Androgen Production

A 58 year old man complains of difficulty in urinating. After routine history and physical examination, a physician diagnosis the man with prostate cancer. The man is treated systemically by intravenous administration a pharmaceutical composition comprising Risperidone and Rumenic acid as disclosed herein. The patient's condition is monitored and after about one month after treatment, the physician determines that the size of the prostate has become smaller. At three and six month check-ups, the physician determines that there is a further decrease in the size of the tumor and that serum PSA levels are within the normal range. This reduction in tumor size and/or reduces serum PSA levels indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, a chemotherapeutic agent, an anti-proliferative agent, or any combination thereof may be used in the treatment of this cancer.

A 67 year old man previously treated for prostate cancer with a hormone depletion therapy complains of a return of symptoms such as difficulty in urination. After routine history and physical examination, a physician determines that the cancer in the prostate has increase in mass and has metastasized into the bones. The physician diagnosis the man with a hormone refractory prostate cancer. The man is treated systemically by intravenous administration a pharmaceutical composition comprising Risperidone and Rumenic acid as disclosed herein. The patient's condition is monitored and after about one month after treatment, the physician determines that the size of the prostate has not increased in size. At three and six month check-ups, the physician determines that there is a decrease in the size of the tumor and that serum PSA levels are within the normal range. This reduction in tumor size and/or reduces serum PSA levels indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, a chemotherapeutic agent, an anti-proliferative agent, or any combination thereof may be used in the treatment of this cancer.

A 61 year old woman complains of a solid mass in her left breast. After routine history and physical examination, a physician diagnosis the woman with breast cancer. The woman is treated systemically by oral administration a pharmaceutical composition comprising Risperidone and Rumenic acid as disclosed herein. The patient's condition is monitored and after about one month after treatment, the physician notes that the growth of the mass has slowed down. At three and six month check-ups, the physician determines that there is a decrease in the size of the tumor. The reduction in tumor size indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, a chemotherapeutic agent, an anti-proliferative agent, or any combination thereof may be used in the treatment of this cancer.

A 53 year old woman complains of pelvic pain. After routine history and physical examination, a physician diagnosis the woman with ovarian cancer. The woman is treated systemically by oral administration a pharmaceutical composition comprising Risperidone and Rumenic acid as disclosed herein. The patient's condition is monitored and after about one month after treatment, the physician notes that the growth of the malignant tumor has slowed down. At three and six month check-ups, the woman indicates that the pelvic pain is much reduced and the physician determines that there is a decrease in the size of the tumor. The reduction in pain and/or tumor size indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, a chemotherapeutic agent, an anti-proliferative agent, or any combination thereof may be used in the treatment of this cancer.

A 69 year old man complains of chest pain and that it is difficult to breath and wheezing. After routine history and physical examination, a physician diagnosis the man with lung cancer. The man is treated systemically by intravenous administration a pharmaceutical composition comprising Risperidone and Rumenic acid as disclosed herein. The patient's condition is monitored and after about one month after treatment, the physician notes that the growth of the malignant tumor has slowed down. At three and six month check-ups, the man indicates that the chest pain is reduced, normal breathing has returned, and the physician determines that there is a decrease in the size of the tumor. The reduction in pain and/or tumor size indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, a chemotherapeutic agent, an anti-proliferative agent, or any combination thereof may be used in the treatment of this cancer.

A 61 year old man complains of abdominal pain. After routine history and physical examination, a physician diagnosis the man with pancreatic cancer. The man is treated systemically by oral administration a pharmaceutical composition comprising Risperidone and Rumenic acid as disclosed herein. The patient's condition is monitored and after about one month after treatment, the physician notes that the growth of the malignant tumor has slowed down. At three and six month check-ups, the man indicates that the abdominal pain is much reduced and the physician determines that there is a decrease in the size of the tumor. The reduction in pain and/or tumor size indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, a chemotherapeutic agent, an anti-proliferative agent, or any combination thereof may be used in the treatment of this cancer.

A 20 year old man begins losing hair on his scalp. After routine history and physical examination, a physician diagnosis the man with androgenic alopecia. The man is treated locally by topical administration a pharmaceutical composition comprising Risperidone and Rumenic acid as disclosed herein. The patient's condition is monitored and after about one month after treatment, the physician notes that further loss of hair has slowed. At three and six month check-ups, the man indicates that he has noticed regrowth in the areas where hair loss occurred on his scalp and physician determines that there is a further decrease in hair loss. This reduction in hair loss and/or new hair growth indicates successful treatment with the composition disclosed herein. In a similar manner, a pharmaceutical composition any of the other benzo(iso)oxazolepiperidines disclosed herein and/or any of the other fatty acids disclosed herein, such as, e.g., an omega-3 fatty acid, an omega-6 fatty acid, an omega-7 fatty acid, an omega-9 fatty acid, or any combination thereof, may be formulated into a pharmaceutical composition and administered to the patient as described above. Additionally, administration of other therapeutic compounds disclosed herein, such as, e.g., a 5α reductase inhibitor, may be used in the treatment of this hair loss.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating an individual with a pancreatic cancer, the method comprising the step of administering to the individual a therapeutically effective amount of risperidone and about 0.01 mg/kg/day to about 0.5 mg/kg/day of 9Z,11E conjugated Linoleic Acid, wherein administration reduces a symptom associated with the pancreatic cancer, thereby treating the individual, wherein there is a synergistic effect between the risperidone and 9Z,11E conjugated Linoleic Acid.

2. The method according to claim 1, the therapeutically effective amount of risperidone is from about 0.1 mg/day to about 20 mg/day.

3. The method according to claim 2, wherein the therapeutically effective amount of risperidone is from about 0.5 mg/day to about 17.5 mg/day.

4. The method according to claim 1, wherein the therapeutically effective amount of risperidone is from about 0.01 mg/kg/day to about 0.5 mg/kg/day.

5. The method according to claim 1, wherein 9Z,11E conjugated Linoleic Acid is in an amount from about 1 mg/day to about 20 mg/day.

6. The method according to claim 5, wherein 9Z,11E conjugated Linoleic Acid is in an amount from 0.5 mg/day to about 17.5 mg/day.

7. The method according to claim 1, wherein risperidone and 9Z,11E conjugated Linoleic Acid are administered sequentially or simultaneously.

8. The method according to claim 1, wherein risperidone and 9Z,11E conjugated Linoleic Acid are administered to the individual as a single composition.

9. The method according to claim 1, wherein the reduced symptom includes a reduction in the frequency of a symptom of a pancreatic cancer, a reduction in the number of symptoms of a pancreatic cancer, or any combination thereof.

10. A method of treating an individual with a pancreatic cancer, the method comprising the step of administering to the individual about 0.01 mg/kg/day to about 0.5 mg/kg/day of risperidone and about 0.01 mg/kg/day to about 0.5 mg/kg/day of 9Z,11E conjugated Linoleic Acid, wherein administration reduces a symptom associated with the pancreatic cancer, thereby treating the individual, wherein there is a synergistic effect between risperidone and the 9Z,11E conjugated Linoleic Acid.

11. The method according to claim 10, wherein risperidone and 9Z,11E conjugated Linoleic Acid are administered sequentially or simultaneously.

12. The method according to claim 10, wherein risperidone and 9Z,11E conjugated Linoleic Acid are administered to the individual as a single composition.

13. A method of treating an individual with a pancreatic cancer, the method comprising the step of administering to the individual about 0.1 mg/day to about 20 mg/day of risperidone and about OA mg/day to about 20 mg/day of 9Z,11E conjugated Linoleic Acid, wherein administration reduces a symptom associated with the pancreatic cancer, thereby treating the individual, wherein there is a synergistic effect between risperidone and the 9Z,11E conjugated Linoleic Acid.

14. The method according to claim 13, wherein risperidone is in an amount from about 0.5 mg/day to about 17.5 mg/day.

15. The method according to claim 13, wherein 9Z,11E conjugated Linoleic Acid is in an amount from about 0.5 mg/day to about 17.5 mg/day.

16. The method according to claim 13, wherein risperidone and 9Z,11E conjugated Linoleic Acid are administered sequentially or simultaneously.

17. The method according to claim 13, wherein risperidone and 9Z,11E conjugated Linoleic Acid are administered to the individual as a single composition.

18. A method of treating an individual with a pancreatic cancer, the method comprising the step of administering to the individual a therapeutically effective amount of risperidone and about 0.1 mg/day to about 20 mg/day of 9Z,11E conjugated Linoleic Acid, wherein administration reduces a symptom associated with the pancreatic cancer, thereby treating the individual, wherein there is a synergistic effect between risperidone and 9Z,11E conjugated Linoleic Acid.

19. The method according to claim 18, wherein the therapeutically effective amount of risperidone is an amount from about 0.1 mg/day to about 20 mg/day.

20. The method according to claim 19, wherein the therapeutically effective amount of risperidone is an amount from about from 0.5 mg/day to about 17.5 mg/day.

21. The method according to claim 18, wherein the therapeutically effective amount of risperidone is an amount from about 0.01 mg/kg/day to about 0.5 mg/kg/day.

22. The method according to claim 18, wherein 9Z,11E conjugated Linoleic Acid is an amount from about from 0.5 mg/day to about 17.5 mg/day.

23. The method according to claim 18, wherein 9Z,11E conjugated Linoleic Acid is an amount from about from 0.01 mg/kg/day to about 0.5 mg/kg/day.

24. The method according to claim 18, wherein risperidone and 9Z,11E conjugated Linoleic Acid are administered sequentially or simultaneously.

25. The method according to claim 18, wherein risperidone and 9Z,11E conjugated Linoleic Acid are administered to the individual as a single composition.

26. The method according to claim 10, wherein risperidone is an amount from about 0.1 mg/day to about 20 mg/day.

27. The method according to claim 26, wherein risperidone is an amount from about 0.5 mg/day to about 17.5 mg/day.

28. The method according to claim 10, wherein 9Z,11E conjugated Linoleic Acid is an amount from about 0.1 mg/day to about 20 mg/day.

29. The method according to claim 28, wherein 9Z,11E conjugated Linoleic Acid is an amount from about 0.5 mg/day to about 17.5 mg/day.

\* \* \* \* \*